(12) United States Patent  (10) Patent No.: US 9,164,995 B2
Grim, III et al.  (45) Date of Patent: Oct. 20, 2015

(54) ESTABLISHING USAGE POLICIES FOR RECORDED EVENTS IN DIGITAL LIFE RECORDING

(75) Inventors: Clifton E. Grim, III, Seabrook, TX (US); Rex Edward Marzke, Houston, TX (US); Mark B. Stevens, Austin, TX (US); Gary A. Ward, Seabrook, TX (US); John David Wilson, Houston, TX (US)

(73) Assignee: International Business Machines Corporation, Armonk, NY (US)

( * ) Notice: Subject to any disclaimer, the term of this patent is extended or adjusted under 35 U.S.C. 154(b) by 1 day.

(21) Appl. No.: 12/347,156

(22) Filed: Dec. 31, 2008

(65) Prior Publication Data
US 2009/0177700 A1  Jul. 9, 2009

Related U.S. Application Data

(63) Continuation-in-part of application No. 11/968,772, filed on Jan. 3, 2008.

(51) Int. Cl.
*G06F 17/30* (2006.01)
*G06Q 10/10* (2012.01)
*G11B 27/30* (2006.01)
(Continued)

(52) U.S. Cl.
CPC .... *G06F 17/30026* (2013.01); *G06F 17/30032* (2013.01); *G06F 17/30035* (2013.01); *G06F 17/30041* (2013.01); *G06F 17/30044* (2013.01); *G06F 17/30817* (2013.01); *G06Q 10/10* (2013.01); *G11B 27/3027* (2013.01);
(Continued)

(58) Field of Classification Search
CPC .................................................. H04N 21/4627
USPC .......................................................... 386/200
See application file for complete search history.

(56) References Cited

U.S. PATENT DOCUMENTS 6,049,787 A   4/2000   Takahashi et al.
6,301,370 B1  10/2001  Steffens et al.
(Continued)

FOREIGN PATENT DOCUMENTS

EP   1475967 A1   11/2004
JP   2002297893   10/2002
WO   WO99/49656   9/1999

OTHER PUBLICATIONS

U.S. Appl. No. 11/968,772, filed Jan. 3, 2008, Boomer et al.
(Continued)

*Primary Examiner* — Mahesh Dwivedi
(74) *Attorney, Agent, or Firm* — Yee & Associates, P.C.; Maeve L. McCarthy

(57) ABSTRACT

The illustrative embodiments described herein provide a computer implemented method, apparatus, and computer program product for managing usage policies for data recorded with a digital life recorder. A usage profile sensor determines whether a broadcast of a usage profile is detected. A usage profile sensor receives the broadcast of the usage profile in response to a first determination that the broadcast of the usage profile is detected, wherein the usage profile comprises a usage policy. A usage profile processor determines whether the usage profile is currently being tracked. A usage profile processor records a start date, a start time, and usage profile information into a tracking table in response to a second determination that the usage profile is not currently being tracked.

12 Claims, 27 Drawing Sheets

(51) Int. Cl.
  *H04N 5/76* (2006.01)
  *G06F 19/00* (2011.01)
  *H04N 9/82* (2006.01)

(52) U.S. Cl.
  CPC ............... *H04N 5/76* (2013.01); *G06F 19/322* (2013.01); *H04N 9/8205* (2013.01)

(56) References Cited

U.S. PATENT DOCUMENTS

| | | | |
|---|---|---|---|
| 6,578,014 | B1 | 6/2003 | Murcko, Jr. |
| 6,778,968 | B1 | 8/2004 | Gulati |
| 6,816,842 | B1 | 11/2004 | Singh et al. |
| 6,825,875 | B1 | 11/2004 | Strub et al. |
| 6,947,911 | B1 | 9/2005 | Moritsu et al. |
| 7,024,681 | B1* | 4/2006 | Fransman et al. ............ 725/115 |
| 7,062,472 | B2 | 6/2006 | Dan et al. |
| 7,080,405 | B2 | 7/2006 | Himmel et al. |
| 7,165,036 | B2 | 1/2007 | Kruk et al. |
| 7,200,747 | B2 | 4/2007 | Riedel et al. |
| 7,316,033 | B2 | 1/2008 | Risan et al. |
| 7,446,803 | B2 | 11/2008 | Leow et al. |
| 7,454,019 | B2 | 11/2008 | Williams |
| 7,551,755 | B1 | 6/2009 | Steinberg et al. |
| 7,555,148 | B1 | 6/2009 | Steinberg et al. |
| 7,561,723 | B2 | 7/2009 | Goldberg |
| 7,564,994 | B1 | 7/2009 | Steinberg et al. |
| 7,664,233 | B1* | 2/2010 | Kirchmeier et al. ............ 379/37 |
| 7,894,639 | B2 | 2/2011 | Grim, III et al. |
| 8,005,272 | B2 | 8/2011 | Grim, III et al. |
| 8,010,645 | B2 | 8/2011 | Rao |
| 8,014,573 | B2 | 9/2011 | Boomer et al. |
| 2002/0184196 | A1 | 12/2002 | Lehmeier et al. |
| 2002/0188453 | A1 | 12/2002 | Hirschberg et al. |
| 2003/0071902 | A1 | 4/2003 | Allen et al. |
| 2003/0077074 | A1* | 4/2003 | Okamoto et al. ............... 386/94 |
| 2003/0126596 | A1 | 7/2003 | Kim |
| 2003/0163339 | A1 | 8/2003 | Elliot |
| 2004/0001142 | A1 | 1/2004 | Kumhyr |
| 2004/0024688 | A1* | 2/2004 | Bi et al. .......................... 705/37 |
| 2004/0049571 | A1* | 3/2004 | Johnson et al. ................ 709/224 |
| 2004/0155981 | A1* | 8/2004 | Ichifuji et al. ................ 348/563 |
| 2004/0180683 | A1 | 9/2004 | Dennis et al. |
| 2004/0213437 | A1 | 10/2004 | Howard et al. |
| 2004/0246127 | A1 | 12/2004 | Junqua |
| 2005/0075097 | A1 | 4/2005 | Lehikoinen et al. |
| 2005/0105779 | A1 | 5/2005 | Kamei |
| 2005/0154682 | A1* | 7/2005 | Taylor ............................ 705/71 |
| 2005/0162279 | A1 | 7/2005 | Marshall et al. |
| 2005/0180567 | A1* | 8/2005 | Williams ...................... 380/201 |
| 2005/0182701 | A1* | 8/2005 | Cheston et al. ................. 705/32 |
| 2005/0207622 | A1 | 9/2005 | Haupt et al. |
| 2005/0216274 | A1* | 9/2005 | Kim ............................. 704/276 |
| 2005/0250548 | A1 | 11/2005 | White |
| 2005/0257241 | A1 | 11/2005 | Faulkner et al. |
| 2005/0264412 | A1 | 12/2005 | Levesque et al. |
| 2005/0270178 | A1 | 12/2005 | Ioli |
| 2006/0020630 | A1 | 1/2006 | Stager et al. |
| 2006/0028488 | A1 | 2/2006 | Gabay et al. |
| 2006/0072811 | A1 | 4/2006 | Porter et al. |
| 2006/0089912 | A1* | 4/2006 | Spagna et al. .................. 705/51 |
| 2006/0098088 | A1 | 5/2006 | Raghunath |
| 2006/0156417 | A1* | 7/2006 | Choi .............................. 726/27 |
| 2006/0171453 | A1 | 8/2006 | Rohlfing et al. |
| 2006/0200541 | A1* | 9/2006 | Wikman et al. ................ 709/223 |
| 2006/0222244 | A1 | 10/2006 | Haupt et al. |
| 2006/0224846 | A1 | 10/2006 | Amarendran et al. |
| 2006/0227237 | A1 | 10/2006 | Kienzle et al. |
| 2006/0287014 | A1* | 12/2006 | Matsuura et al. .......... 455/575.2 |
| 2007/0003113 | A1 | 1/2007 | Goldberg |
| 2007/0036395 | A1 | 2/2007 | Okun |
| 2007/0049984 | A1 | 3/2007 | Osypka |
| 2007/0112852 | A1 | 5/2007 | Sorvari et al. |
| 2007/0118372 | A1 | 5/2007 | Wise et al. |
| 2007/0124249 | A1 | 5/2007 | Aerrabotu et al. |
| 2007/0124272 | A1* | 5/2007 | DeCastra et al. ................ 707/1 |
| 2007/0150517 | A1 | 6/2007 | Malone |
| 2007/0228159 | A1 | 10/2007 | Kashiwa et al. |
| 2007/0294273 | A1 | 12/2007 | Bendeck et al. |
| 2007/0296817 | A1* | 12/2007 | Ebrahimi et al. ............. 348/161 |
| 2008/0016193 | A1 | 1/2008 | Allen et al. |
| 2008/0046352 | A1* | 2/2008 | Jung et al. ....................... 705/37 |
| 2008/0046406 | A1 | 2/2008 | Seide et al. |
| 2008/0071561 | A1* | 3/2008 | Holcombe ....................... 705/1 |
| 2008/0130960 | A1 | 6/2008 | Yagnik |
| 2008/0159601 | A1 | 7/2008 | Alberth et al. |
| 2008/0253623 | A1 | 10/2008 | Hauke |
| 2009/0030952 | A1 | 1/2009 | Donahue et al. |
| 2009/0049413 | A1 | 2/2009 | Lehtovirta et al. |
| 2009/0109286 | A1 | 4/2009 | Ennis |
| 2009/0129757 | A1 | 5/2009 | Mori et al. |
| 2009/0171902 | A1 | 7/2009 | MacLaurin et al. |
| 2009/0175599 | A1 | 7/2009 | Grim, III et al. |
| 2009/0295911 | A1 | 12/2009 | Grim, III et al. |

OTHER PUBLICATIONS

U.S. Appl. No. 12/277,804, filed Nov. 25, 2008, Grim, III et al.
U.S. Appl. No. 12/130,549, filed May 30, 2008, Grim, III et al.
U.S. Appl. No. 12/277,873, filed Nov. 25, 2008, Grim, III et al.
U.S. Appl. No. 12/347,182, filed Dec. 31, 2008, Grim, III et al.
Picard, Ken, "Tales from the Cryptographer—Security Guru Bruce Schneider Busts the Myths of Post-9/11 Safety Measures", Jun. 2006, pp. 1-3, Retrieved Sep. 14, 2007, <http://www.schneier.com/news-019.html>.
Ward, Mark, "Log Your Life via Your Phone", BBC News Online, Mar. 2004, pp. 1-3, Retrieved Sep. 14, 2007, <http://news.bbc.co.uk/2/hi/technology/3497596.stm>.
Seward, Liz, "Sensor rise Powers Life Recorders", BBC News Online, Aug. 2007, pp. 1-3, Retrieved Sep. 14, 2007, <http://news.bbc.co.uk/2/hi/technology/6968591.stm>.
Carter, William, "Personal Life Recorder", William Carter Weblog, Sep. 2004, pp. 1, Retrieved Sep. 14, 2007, <http://interactive.usc.edu/members/will/archives/002470.php>.
Fleming, Nic, "Computers 'Could Store Entire Live by 2026'", Dec. 2006, pp. 1, Retrieved Jan. 2, 2008, <http://www.telegraph.co.uk/core/Content/displayPrintabe.jhtml;jsessionid=C3FA511NTKF...>.
Genuth, "Saving Your Life on a Hard Drive", Jun. 2006, pp. 1-6, Retrieved Jan. 2, 2008, <http://www.tfpt.info/articles.php?itemId=16/>.
"Welcome", Streav, pp. 1, Retrieved Jan. 2, 2008, <http://streav.sorceforge.net/>.
Vemuri, Sunil, "What Was I Thinking?", Electronic Publishing Group, pp. 1-6, Retrieved Jan. 2, 2008 <http://web.media.mit.edu/~vemuri/wwit/wwit-overview.html>.
Yasuhiko, Naito, "A Role of Advanced Image Data Logger Systems in Marine Animal Studies", Coast Marine Science, vol. 30, No. 2, Feb. 21, 2006, pp. 407-413, Japan, retrieved from the Internet: URL: http://repository.dl.itc.u-tokyo.ac.jp/dspace/bitstream/2261/5663/1/KJ00004354639.pdf.
"Youtube—Broadcast Yourself" Internet Citation, XP002441767, retrieved from the Internet: URL: http://web.archive.org/web/20051001143606/http://ww.youtube.com, Oct. 2005.
Ting, J. S. L, et al, "A Dynamic RFID-Based Mobile Monitoring System in Animal Care Management Over a Wireless Network", Wireless Communications, Networking and Mobile Computing, 2007, WICOM 2007, International Conference on, IEEE, Piscataway, NJ, USA, Sep. 21, 2007, pp. 2085-2088.
Healey, Jennifer et al, "Startle Cam: A Cybernetic Wearable Camera", Wearable Computers, 1998. Digest of Papers, Second International Symposium in Pittsburgh, PA, USA, Oct. 19-20, 1998, Los Alamitos, CA, USA, IEEE Comput. SOC, US, Oct. 19, 1998, pp. 42-49.
Frederick, "Surveillance Video Face Recognition (SVFR)", dated Nov. 2007.
Hartnell-Young et al., Article entitled "Lifeblog: A new Concept in Mobile Learning", dated Nov. 2005.
USPTO office action for U.S. Appl. No. 11/768,772 dated Mar. 17, 2010.

(56) References Cited

OTHER PUBLICATIONS

USPTO office action for U.S. Appl. No. 12/277,804 dated Jun. 1, 2010.
USPTO office action for U.S. Appl. No. 12/347,182 dated May 28, 2010.
USPTO Final Office Action for U.S. Appl. No. 12/347,182 dated Oct. 27, 2010.
USPTO Notice of allowance for U.S. Appl. No. 12/277,804 dated Oct. 15, 2010.
USPTO Office Action for U.S. Appl. No. 11/968,772 dated Nov. 23, 2010.
USPTO Notice of allowance for U.S. Appl. No. 11/968,772 dated Apr. 19, 2011.
USPTO office action for U.S. Appl. No. 12/347,182 dated Feb. 2, 2011.
USPTO Notice of allowance for U.S. Appl. No. 12/347,182 dated Apr. 20, 2011.
USPTO Office Action dated Jul. 18, 2011, regarding U.S. Appl. No. 12/130,549.
Dumais et al., "Stuff I've Seen: A System for Personal Information Retrieval and Re-Use," SIGIR '03: Proceedings of the 26th annual international ACM SIGIR conference on Research and development in informaion retrieval, Jul.-Aug. 2003, pp. 72-79.
Gemmell et al., "MyLifeBits: Fulfilling the Memex Vision (PDF)," ACM Multimedia, Association for Computing Machinery, Inc., Dec. 2002, pp. 235-238.
USPTO Non-final office action dated May 17, 2010 regarding U.S. Appl. No. 11/968,772.
USPTO Final office action dated Aug. 31, 2010 regarding U.S. Appl. No. 11/968,772.
Final Office Action, dated Dec. 13, 2011, regarding U.S. Appl. No. 12/130,549, 20 pages.
Office Action, dated Apr. 3, 2012, regarding U.S. Appl. No. 12/277,873, 39 pages.
Office Action, dated Feb. 14, 2013, regarding U.S. Appl. No. 12/277,873, 21 pages.
Final Office Action dated Aug. 30, 2013 regarding U.S. Appl. No. 12/277,873, 17 pages.
Office Action, dated Dec. 19, 2013, regarding U.S. Appl. No. 12/277,873, 16 pages.
Final Office Action, dated May 21, 2014, regarding U.S. Appl. No. 12/277,873, 14 pages.
Notice of allowance dated Mar. 30, 2015, regarding U.S. Appl. No. 12/277,873, 13 pages.

* cited by examiner

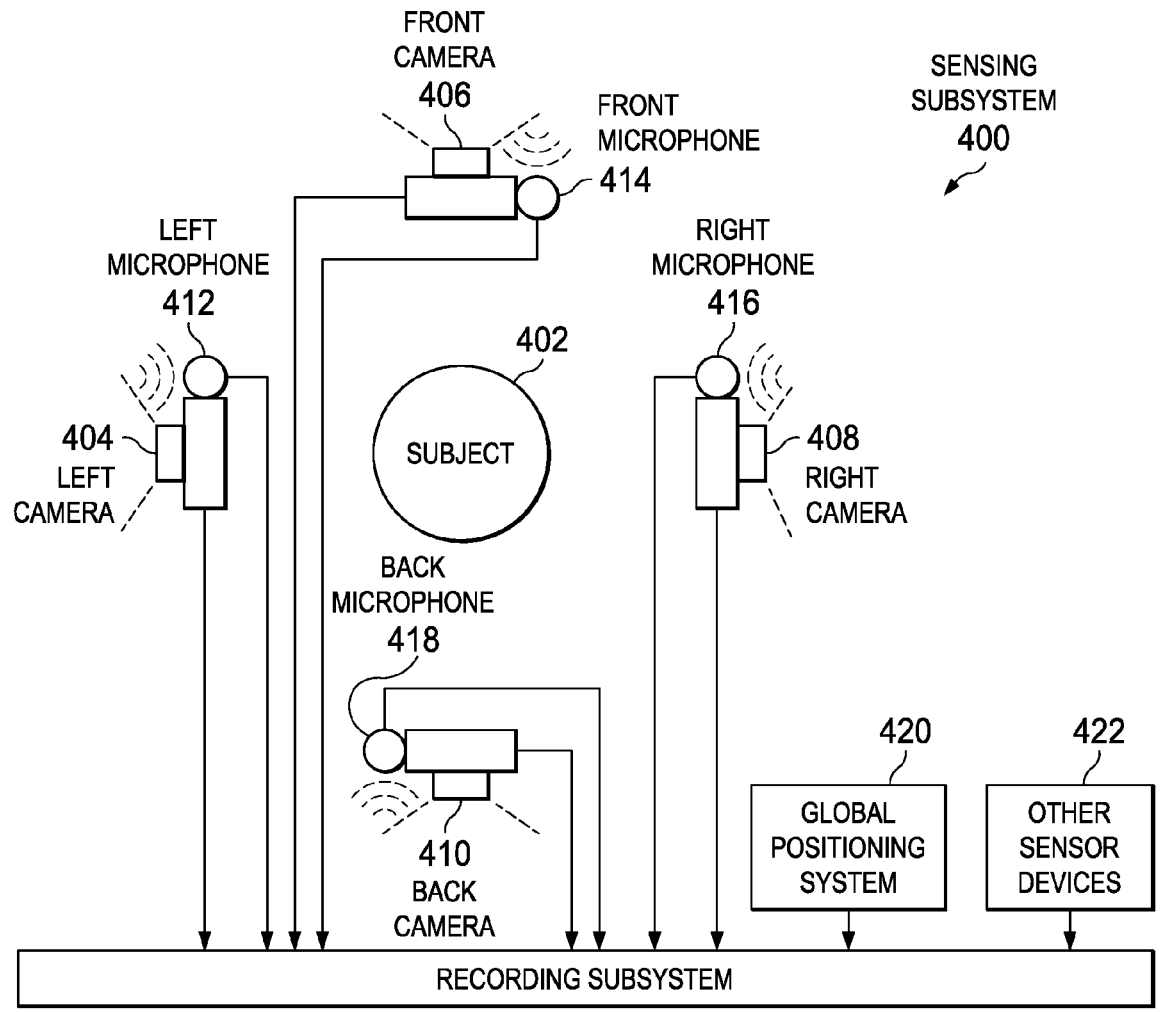
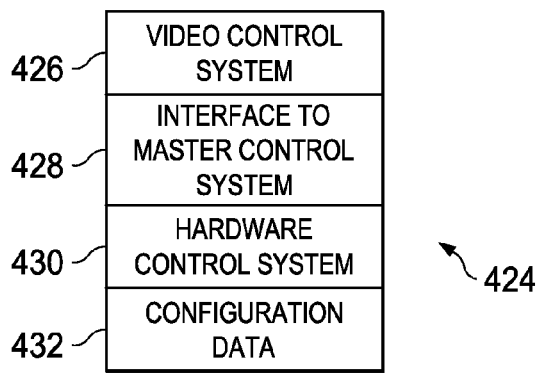
FIG. 4

ESTABLISHING USAGE POLICIES FOR RECORDED EVENTS IN DIGITAL LIFE RECORDING

This application is a continuation-in-part of application Ser. No. 11/968,772, filed Jan. 3, 2008.

BACKGROUND OF THE INVENTION

1. Field of the Invention

The present invention relates generally to an improved data processing system, and in particular, to a method and apparatus for processing data. Still more particularly, the present invention relates to a computer implemented method, apparatus, and computer program product for managing usage policies for data recorded with a digital life recorder.

2. Description of the Related Art

Advancements in technology have drastically changed the way people do things. Gone are the days of printed encyclopedias. These paper-based resources have been replaced by a plethora of information readily available on the World Wide Web. Instead of taking a roll of film to a photo shop to be developed, digital images are stored on computers, laptops, and in digital photo frames. Additionally, because snapping a digital photograph or taking a digital video costs virtually nothing, more digital photos and videos are taken than was previously taken by conventional means. The digital images represent memories of special or even obscure events. However, searching for a particular digital image from the collection of digital images stored on a computer is a difficult task. In addition, numerous events in our daily lives are never captured on film. Furthermore, photos do not capture the spoken words, feelings, or environmental factors associated with everyday activities.

Accordingly, there exists a need for a mechanism for dynamically capturing, storing, and presenting data associated with all aspects of daily activities in an efficient manner.

BRIEF SUMMARY OF THE INVENTION

The illustrative embodiments described herein provide a computer implemented method, apparatus, and computer program product for managing usage policies for data recorded with a digital life recorder. A usage profile sensor determines whether a broadcast of a usage profile is detected. A usage profile sensor receives the broadcast of the usage profile in response to a first determination that the broadcast of the usage profile is detected, wherein the usage profile comprises a usage policy. A usage profile processor determines whether the usage profile is currently being tracked. A usage profile processor records a start date, a start time, and usage profile information into a tracking table in response to a second determination that the usage profile is not currently being tracked.

BRIEF DESCRIPTION OF THE SEVERAL VIEWS OF THE DRAWINGS

FIG. 4 is a diagram depicting components of a sensing subsystem in accordance with an illustrative embodiment;

DETAILED DESCRIPTION OF THE INVENTION

Figure 1:
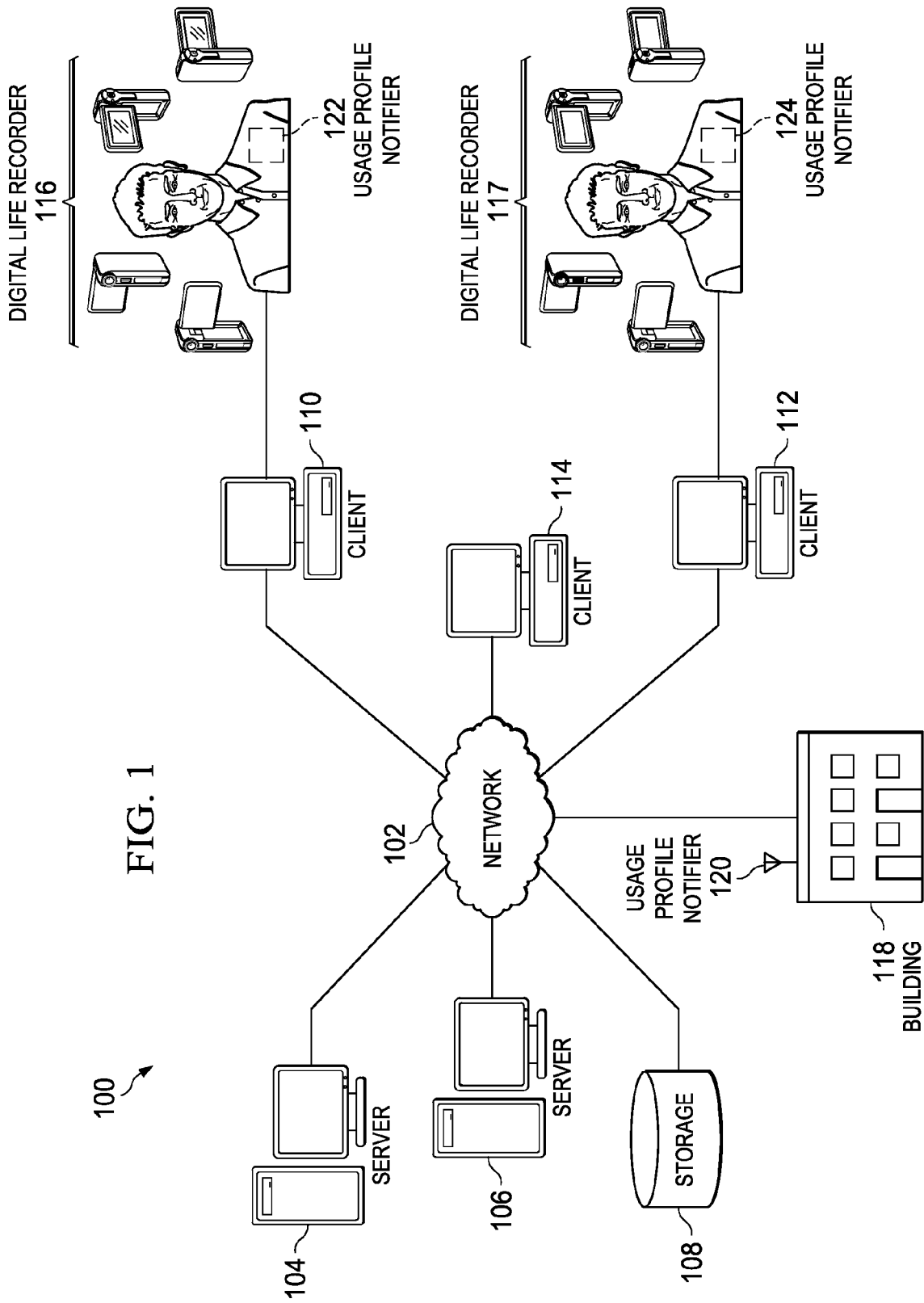
FIG. 1 is a pictorial representation of a network of data processing systems in which illustrative embodiments may be implemented.

As will be appreciated by one skilled in the art, the present invention provides a system, method, or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media, such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including, but not limited to wireless, wireline, optical fiber cable, RF, etc.

Computer program code for carrying out operations of the present invention may be written in any combination of one or more programming languages, including an object oriented programming language, such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Figure 2:
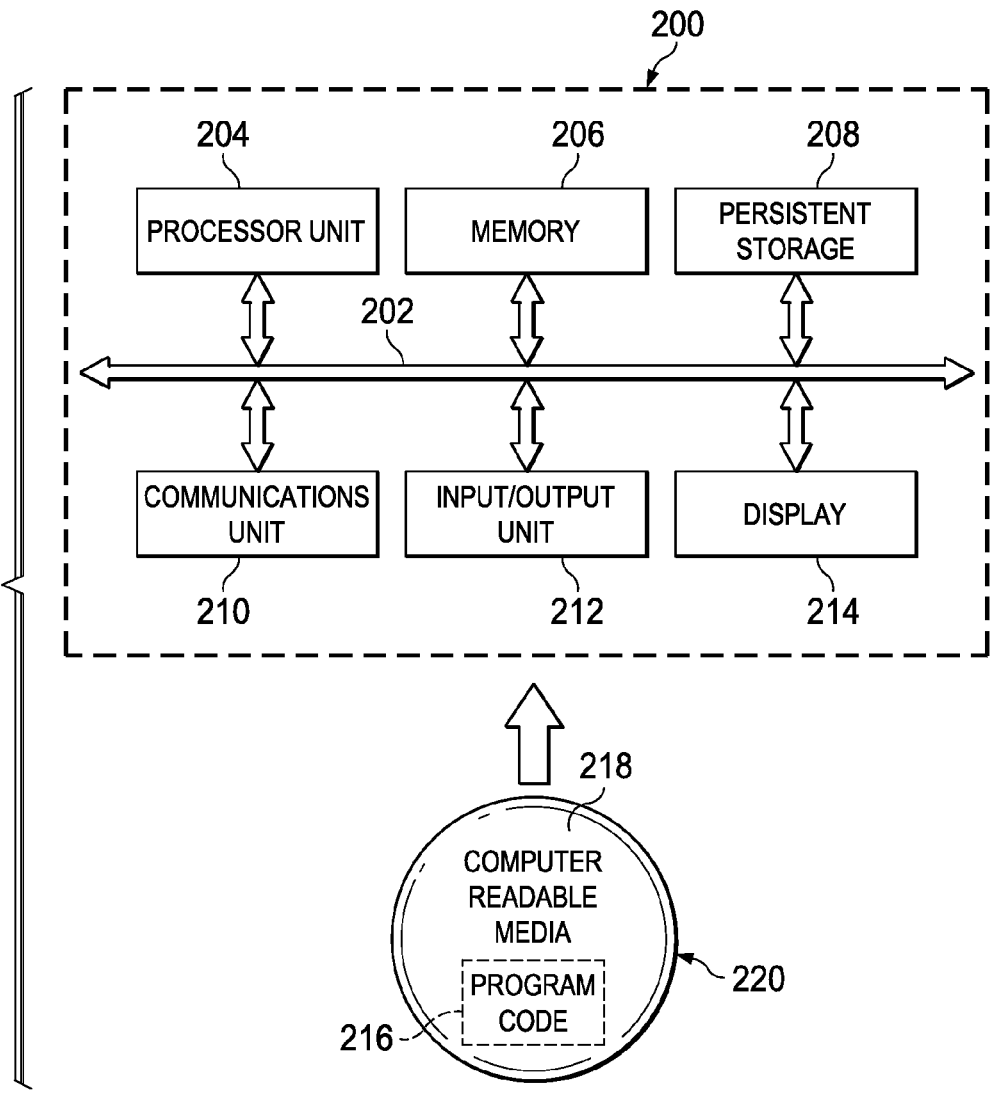
FIG. 2 is a block diagram of a data processing system in which illustrative embodiments may be implemented.

With reference now to the figures, and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 is a pictorial representation of a network of data processing system in which illustrative embodiments may be implemented. Network data processing system 100 is a network of computers in which embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. These clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. The illustrative embodiments may be implemented in a data processing system, such as clients 110, 112, and 114. Clients 110, 112, and 114 may use an Internet browser to communicate with server 104. Network data processing system 100 may include additional servers, clients, and other devices not shown.

The illustrative embodiments may be used as a digital life recorder for capturing still images, video, audio, biometric information and other types of data associated with the daily activities of a person. The activities may be recorded on a continuous basis or may be periodically captured. For example, FIG. 1 depicts recording subsystem 116. Recording subsystem 116 receives data captured from a plurality of data capturing devices. The data capturing devices may include, but are not limited to, video cameras. The captured data is processed by a mobile device associated with the person and is stored as raw data within a cache of the mobile device. Upon interfacing with a repository mass store, such as client 110, the stored data within the cache of the mobile device is uploaded to the repository mass store. Client 110 manages the data within the repository mass store and presents the data in response to a user request. Additional details of recording subsystem 116 and the repository mass store will be described below.

Data processing system 100 may also include additional digital life recording systems, such as digital life recorder 117. From the perspective of digital life recorder 116, digital life recorder 117 is a peer digital life recording system. A peer digital life recording system is a digital life recording system in a presence of another digital life recording system.

The components of network data processing system 100 may be configured for acquisition of a usage profile by a user of a digital life recorder, such as digital life recorder 116. Digital life recorder 116 may be updated by retrieving usage profile data from usage profile notifiers 120 and 124. The usage profile notifiers 120, 122, and 124 may include, for example, peer digital life recorder 122 and 124, building 120, a street, a house, or a band. Digital life recorder 117 is a peer digital life recorder to digital life recorder 116. Other mobile devices like phones or video cameras may also be sources of usage profile notifiers.

Network 102 may be, without limitation, a local area network (LAN), wide area network (WAN), Internet, Ethernet, or Intranet. In this example, network 102 is the Internet, representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for different embodiments.

FIG. 2 is a block diagram of a data processing system in which illustrative embodiments may be implemented. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communication links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer readable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

The different components illustrated for data processing system 200 are not meant to provide architectural limitations to the manner in which different embodiments may be implemented. The different illustrative embodiments may be implemented in a data processing system including components in addition to, or in place of, those illustrated for data processing system 200. Other components shown in FIG. 2 can be varied from the illustrative examples shown.

As one example, a storage device in data processing system 200 is any hardware apparatus that may store data. Memory 206, persistent storage 208 and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

The illustrative embodiments described herein provide a computer implemented method, apparatus, and computer program product for managing data. A plurality of data capturing devices dynamically captures data associated with the daily activities of a person. The data is processed using a mobile device associated with the person. As depicted in FIG. 1, clients 110, 112, and 114 may represent a mobile device. The data is stored into a cache of the mobile device. The data stored in the cache of the mobile device is uploaded into a repository mass store in response to interfacing the mobile device with the repository mass store. Interfacing may occur over a network, such as network 102 as shown in FIG. 1. Network 102 may comprise of a wired or wireless communication link. The repository mass store may be associated with a data processing system such as data processing system 200. A selected data segment stored in the repository mass store is presented in response to receiving a request for the selected data segment.

Figure 3:
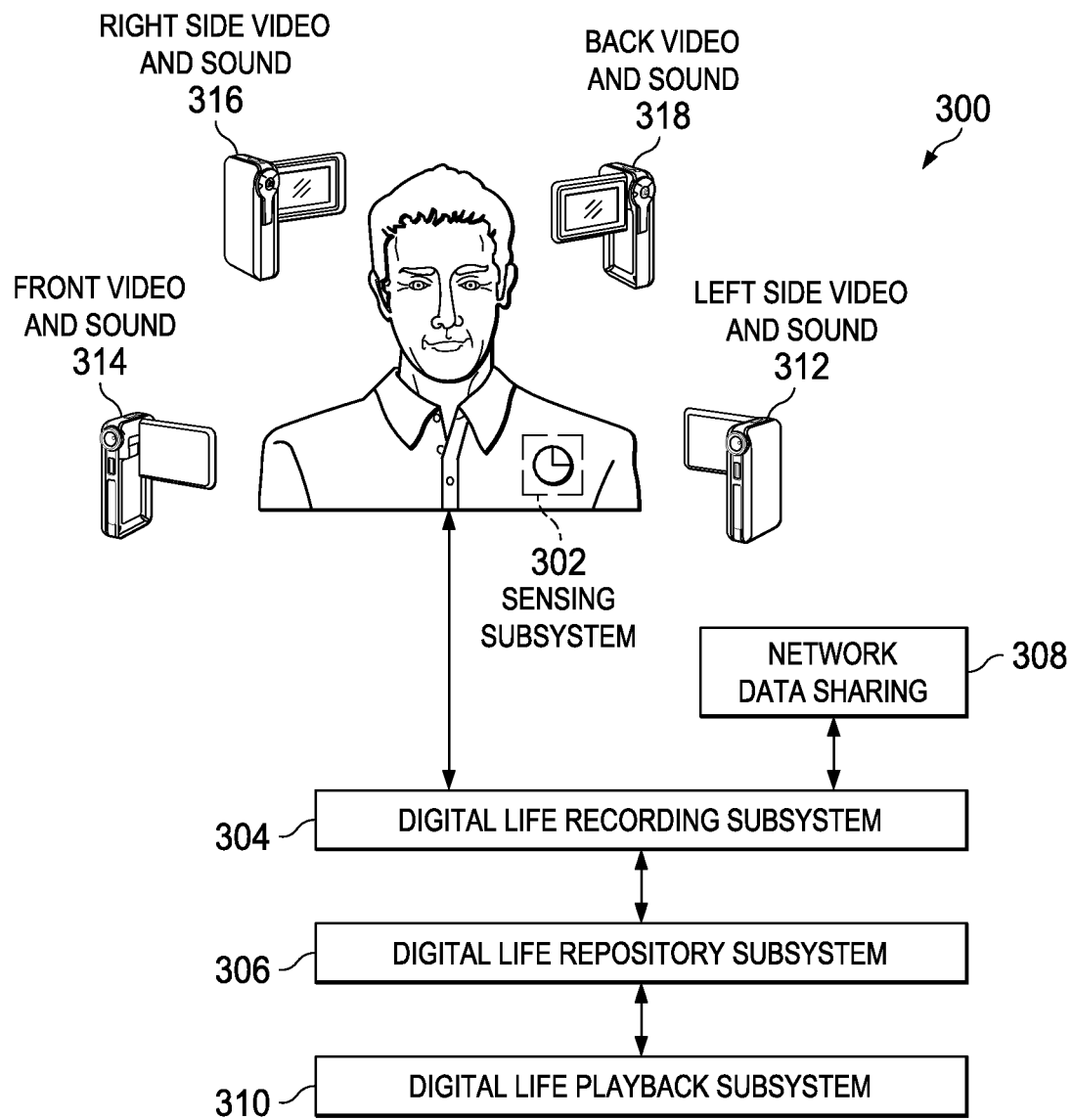
FIG. 3 is a diagram depicting components of a digital life recorder in accordance with an illustrative embodiment.

FIG. 3 is a diagram depicting components of a digital life recorder in accordance with an illustrative embodiment. In this example, digital life recording system 300 comprises of sensing subsystem 302, digital life recording subsystem 304, digital life repository subsystem 306, network data sharing 308, and digital life playback subsystem 310. Sensing subsystem 302 and digital life recording subsystem 304 may be implemented in a recording subsystem, such as recording subsystem 116 as shown in FIG. 1. Digital life repository subsystem 306, network data sharing 308, and digital life playback subsystem 310 may be implemented in a data processing system, such as data processing system 200 as shown in FIG. 2 and client 110 as shown in FIG. 1.

Sensing subsystem 302 comprises of data capturing devices for capturing data. The data capturing devices may comprise, for example, without limitation, video capturing devices, audio capturing devices, biometric capturing devices, global positioning devices, environmental sensor devices, and other suitable devices for digital life recording. The data captured by the devices of subsystem 302 is referred to as digital life recording data.

As depicted in FIG. 3, the video capturing devices are positioned on the person to capture a 360 degree field of view around the person. Additionally, a set of audio capturing devices may be positioned around the person. In this illustrative embodiment, the audio and video capturing devices comprise of left side video and sound 312, front video and sound 314, right side video and sound 316, and back video and sound 318. A set of biometric sensors captures physiological data associated with the person, such as, but not limited to, the heart rate of the person. A set, as referenced herein, may be comprised of one or more objects. Global positioning system devices coupled to the person captures the location and the precise time that data is captured. A set of environmental sensor devices captures environmental variables, such as, but not limited to, temperature, wind speed, barometric pressure, and humidity. In addition, the set of environmental sensor devices may detect environmental hazards, such as, but not limited to, detecting the electric field, radiation, and carbon monoxide. Other data capturing devices that may be associated with the person may include, but are not limited to, medical devices, cellular telephones, and radio-frequency identification devices.

The data capturing devices for capturing data may be hidden in common apparel such as glasses, a hat, clothing or jewelry. In another illustrative embodiment, some or all of the capturing devices may be medically implanted into the person's body.

Sensing subsystem 302 also comprises of a computer for processing the data captured by the devices into a raw data queue. Further details of sensing subsystem 302 are described in FIG. 4 below.

Sensing subsystem 302 transmits the raw data captured by the data capturing devices to digital life recording subsystem 304. Digital life recording subsystem 304 processes the raw data into a processed data queue and stores the data from the processed data queue into a daily cache of a mobile device associated with the person. The details of digital life recording subsystem 304 will be described in FIG. 5.

Digital life repository subsystem 306 manages the long term storage and cataloging of the information representing the person's "digital life" that accumulates over time. On a periodic basis, digital life repository subsystem 306 interfaces with digital life recording subsystem 304 and uploads data stored in the cache of the mobile device. Additionally, details of digital life repository subsystem 306 will be described in FIG. 6.

Network data sharing 308 is a component of digital life recording system 300. Network data sharing 308 provides functions, such as aggregating, organizing, formatting, and attaching metadata to data acquired via public, inter-personal and intra-personal data sharing networks. The resultant aggregate is fed into digital life recording subsystem 304 in these examples. Network data sharing 308 is further described in FIG. 7 below.

Digital life playback subsystem 310 is responsible for the user interface that organizes and presents the information, stored in digital life repository subsystem 306, to a user for review and further processing. Additional details of digital life playback subsystem 310 will be described in FIG. 8.

FIG. 4 is a diagram depicting components of a sensing subsystem in accordance with an illustrative embodiment. Sensing subsystem 400 comprises of a plurality of data capturing devices associated with subject 402. Subject 402 can be, for example, a person or an animal.

In this illustrative example, the data capturing devices comprise of left camera 404, front camera 406, right camera 408, and back camera 410. Additionally, left microphone 412, front microphone 414, right microphone 416, and back microphone 418 are used for capturing audio data. Global positioning system 420 and other sensor devices 422 may also be associated with subject 402. Other sensor devices 422 may include, but are not limited to, a set of biometric devices and a set of environmental sensor devices.

Data model 424 depicts the software components associated with managing sensing subsystem 400. Data model 424 comprises of a video control system 426, an interface to master control system 428, a hardware control system 430, and configuration data 432. The data captured by the data capturing devices is transmitted to a recording subsystem, as will be described below in FIG. 5.

Figure 5:
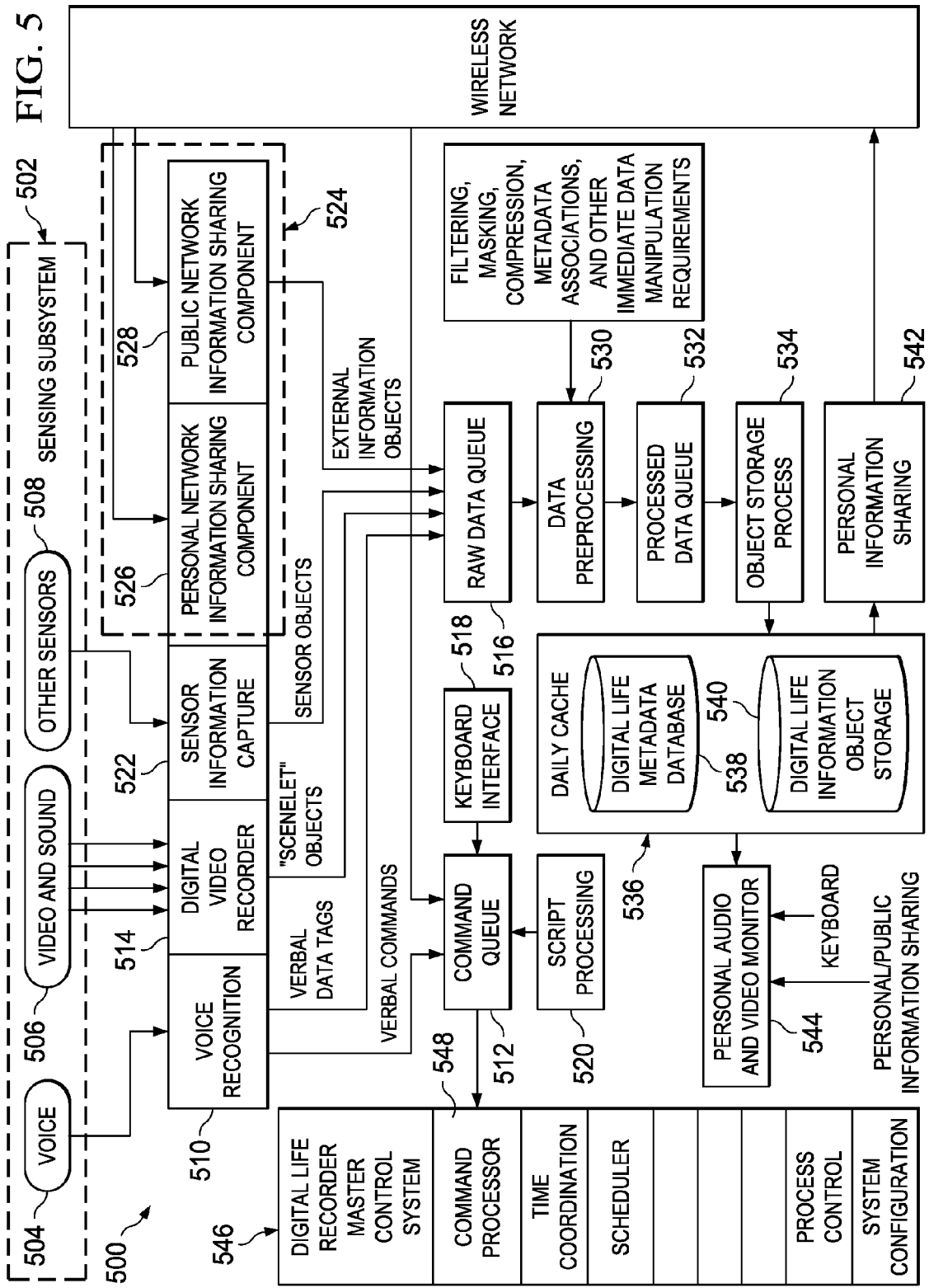
FIG. 5 is a block diagram illustrating the data flow between components of a sensing subsystem and the components of a recording subsystem in accordance with an illustrative embodiment.

FIG. 5 is a block diagram illustrating the data flow between components of a sensing subsystem and the components of a recording subsystem in accordance with an illustrative embodiment. The components of recording subsystem 500 may be implemented in a data processing system, such as data processing system 200 as shown in FIG. 2.

Recording subsystem 500 processes inputs and commands from all the different sources and stores the data in a daily cache. In this illustrative example, recording subsystem 500 comprises of a voice recognition component 510, a command queue 512, a digital video recorder 514, a raw data queue 516, a keyboard interface 518, a script processing 520, a sensor information capture 522, a data preprocessing component 530, a processed data queue 532, an object storage process 534, and a daily cache 536.

Recording subsystem 500 receives input from sensing subsystem 502. Sensing subsystem 502 depicts inputs received from data capturing devices in accordance with an illustrative embodiment of a sensing subsystem, such as sensing subsystem 302 in FIG. 3. Sensing subsystem 502 is responsible for capturing video and sound, voice commands, time and location, environmental details like temperature, biometric information, and any other information that can be imagined to be useful and for which sensors exist. In this example, inputs captured by sensing subsystem 502 includes voice input 504, video and sound input 506, and input from other sensors 508.

Digital life recorder master control system 546 directs the control of sensing subsystem 502. Master control system 546 passes the captured data on to recording subsystem 500 for further processing.

Recording subsystem 500 sends data received from voice input 504 to voice recognition component 510. Voice recognition component 510 processes the data received from voice input 504 to interpret voice commands. The voice commands are forwarded to command queue 512. Command queue 512 may also receive other types of input, such as, but not limited to, input from a cellular phone (not depicted), keyboard interface 518, or inputs received from script processing 520. A script is a set of commands written in an interpreted language to automate certain application tasks. Command queue 512 sends commands to master control system 546. These commands are executed by a command processor 548. The commands can be used to get feedback through headphones and/or display and allows the user to control and configure the system in near real-time.

Recording subsystem 500 passes data from video and sound input 506 to digital video recorder 514. Digital video recorder 514 converts analog data to digital data and organizes the data into data segments. Digital video recorder 514 also takes in metadata from the data capturing devices. Metadata is data that describes the content, quality, condition, origin, and other characteristics of data. The metadata includes a timestamp and location captured by a global positioning system device, such as global positioning system 418 shown in FIG. 4.

The data segments are tagged with the timestamp and location of when and where each data segment was captured prior to sending the data segments to raw data queue 516. In addition, data is captured from other sensors 508 and processed by sensor information capture 522 prior to relaying the data to raw data queue 516.

Additionally, raw data queue 516 includes external information data gathered from network data sharing component 524. Network data sharing component 524 aggregates, organizes, formats, and attaches metadata to data acquired via public, inter-personal and intra-personal data sharing networks. Network data sharing component 524 includes personal network information sharing component 526 and public network information sharing component 528. Network data sharing component 524 is described in more detail in FIG. 7 below.

Data preprocessing component 530 filters, masks, compresses, applies metadata associations, and processes other immediate data manipulation functions. Data preprocessing component 530 reads information from raw data queue 516 and passes the preprocessed data along to processed data queue 532. Recording subsystem 500 uses processed data queue 532 to temporarily store the data before passing the data along to object storage process 534. Object storage process 534 places the data into daily cache 536. The data is placed into two separate databases within daily cache 536; digital life metadata database 538 and digital life information object database 540. Daily cache 536 has enough storage capacity to hold the captured data until recording subsystem 500 interfaces with a repository mass store.

Figure 7:
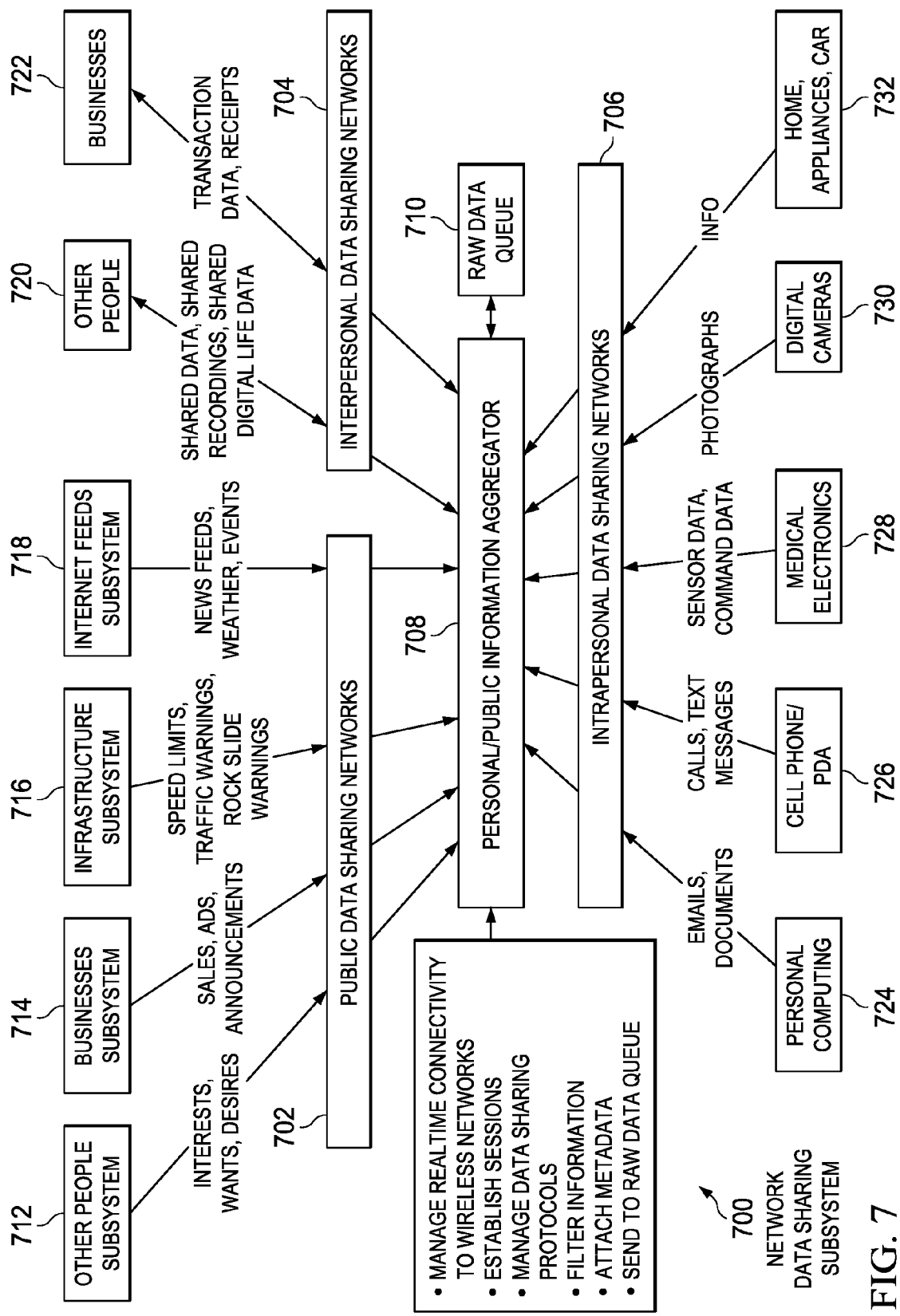
FIG. 7 is a block diagram illustrating the relationship between components of a network data sharing subsystem in accordance with an illustrative embodiment.

Recording subsystem 500 uses a personal information sharing subsystem 542, as will be further described in FIG. 7, to broadcast information from digital life metadata database 538 and digital life information object database 540, within daily cache 536, to authorized users via a wireless or Bluetooth network. Recording subsystem 500 also uses a personal audio and video monitor subsystem 544 to provide a user interface to the data in daily cache 536. Recording subsystem 500 provides a keyboard, which can be used to enter commands and access the user interface functions. Recording subsystem 500 also provides a method to describe and connect to network data sharing component 524.

Figure 6:
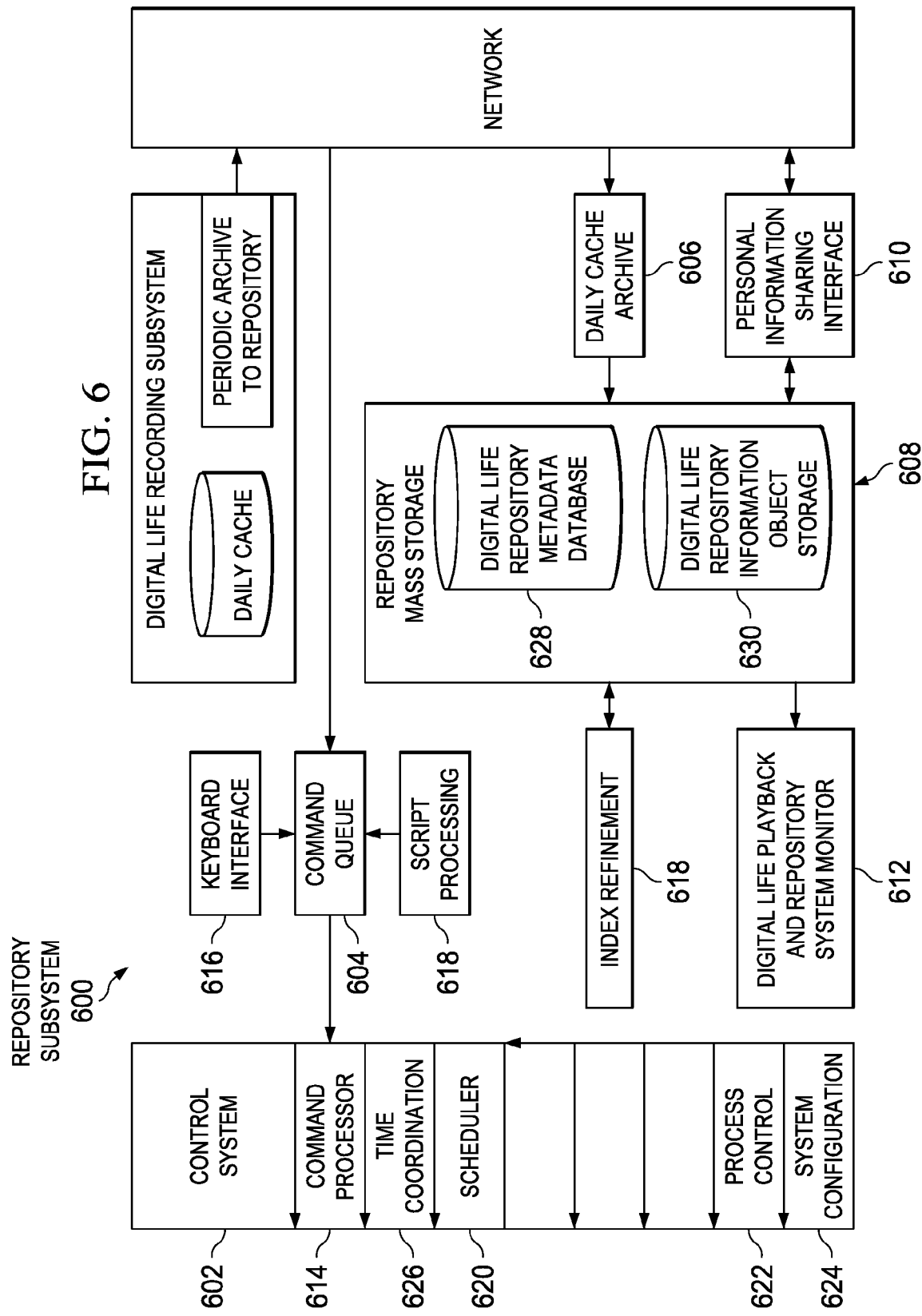
FIG. 6 is a block diagram illustrating the relationship between components of a recording subsystem and the components of a repository subsystem in accordance with an illustrative embodiment.

FIG. 6 is a block diagram illustrating the relationship between components of a recording subsystem and the components of a repository subsystem in accordance with an illustrative embodiment. The recording subsystem may be, for example, recording subsystem 500 shown in FIG. 5. The components of repository subsystem 600 illustrated in FIG. 6 may be implemented in a data processing system, such as data processing system 200 as shown in FIG. 2.

Repository subsystem 600 includes control system 602, command queue 604, network interface (not depicted), a relational storage means called the repository (repository database 608), personal information sharing interface 610, and an interface to the playback subsystem (Digital Life Playback and Repository System Monitor 612).

Control system 602 contains command processor 614 which interprets and executes commands generated by either keyboard interface 616, remote operation via the network, or scripts which are executed (script processing 618) according to a scheduler 620. In addition, control system 602 manages, processes and threads (process control 622), system configuration 624, and time coordination 626.

Recording subsystem 500, as shown in FIG. 5, interfaces with a network, such as network 102 shown in FIG. 1, to upload data stored in the daily cache to repository subsystem 600. Repository subsystem 600 interfaces to the network to download daily cache archive 606 previously stored by the recording subsystem.

Repository subsystem 600 stores the data into repository database 608. Repository database 608 includes two databases, digital life repository metadata database 628 and digital life repository information object storage 630, for long term storage and use. Digital life repository information object storage 630 stores the captured life data objects. Digital life repository metadata database 628 stores metadata used to index and describe the actual captured information objects that the Digital Life Recording Subsystem acquires during the life recording process. Additionally, repository database 608 may include information obtained through personal information sharing interface 610. Additional details of the network data sharing subsystem are described in more detail in FIG. 7 below.

On an ongoing basis, the indexing information in digital life repository metadata database 628 may be enhanced and refined by processes that study the capture data in the repository and update the index information (Ongoing Data and Index Refinement 618). An example of the refinement process includes analyzing audio data within an object to recognize words associated with the captured object. These words are then used as part of a full text search capability where the identified words are used as index information that points to the data objects that contains those words.

An interface, such as digital life playback and repository system monitor 612, exists between repository subsystem 600 and a playback subsystem. Digital life playback and repository system monitor 612 allows the playback subsystem to access the data existing in repository database 608 based on various searching techniques. The playback subsystem manages displaying of the data to a user. Digital life playback and repository system monitor 612 also manages the status and manipulation of repository subsystem 600. Additional details of a playback subsystem are described in more detail in FIG. 8 below.

FIG. 7 is a block diagram illustrating the relationship between components of a network data sharing subsystem in accordance with an illustrative embodiment. The components of network data sharing subsystem 700 illustrated in FIG. 7 may be implemented in a data processing system, such as data processing system 200 as shown in FIG. 2.

Network data sharing subsystem 700 includes public data sharing network 702, interpersonal data sharing network 704, intrapersonal data sharing network 706, and a personal/public information aggregator 708.

Public data sharing network 702 provides connectivity to information that is being locally broadcast as well as predefined Internet feeds. The system may be composed of wireless networks configured to connect automatically when detected. Hard networks may also be used to capture additional information.

Additionally, public data sharing network 702 captures nearby information, from other people broadcasting information about themselves via the other people subsystem 712. This information might be information about their interests and desires. Public data sharing network 702 also captures business information from nearby business broadcasts, such as, but not limited to, sales and advertisements via businesses subsystem 714.

Additionally, public data sharing network 702 captures public and private infrastructure broadcasts via infrastructure subsystem 716. The public and private infrastructure information may include, but are not limited to, speed limits, traffic conditions/warnings, and weather condition warnings. Public data sharing network 702 supports any network connectivity that allows Internet access via Internet Feeds subsystem 718. Internet Feeds subsystem 718 is used to receive web based information, such as, but not limited to, news, weather, entertainment, and sports results.

Interpersonal data sharing network 704 is more specific to the person being monitored than is public data sharing network 702. Interpersonal data sharing network 704 does not receive broadcasts. Instead, interpersonal data sharing network 704 negotiates connections with Other People 720 and Businesses 722 to receive transaction oriented information for recording. For example, transaction information associated with transactions that occur between businesses and the person are recorded. The transaction information may include information about purchases, such as, but not limited to, price, model numbers, serial numbers, warranties, and receipts. Information shared from other people's digital life recording system is captured using a subsystem, such as other people 720.

Intrapersonal data sharing network 706 aggregates personal information about the person's life for recording. The personal information may be aggregated from a plurality of sources including, but not limited to, personal computing 724, cell phone/personal digital assistants (PDA) 726, medical electronics 728, digital cameras 730, and home appliances/car 732. The information captured from personal computing 724 may include, but is not limited to, emails, computer files, computer-based communications like instant messages or voice over IP (VOIP). Bluetooth or other wireless/wired connectivity may be used for interfacing the data to the digital life recorder.

Intrapersonal data sharing network 706 may also capture cell phone conversations and PDA usage from cell phone/PDA 726 using Bluetooth connectivity or other transmission means. Additionally, intrapersonal data sharing network 706 may record the command and data associated with medical electronics 728. Images may also be captured from digital cameras 730. Digital cameras 730 include cameras that are not already associated with the sensing subsystem. Other data may include information associated with home appliances/car 732.

Personal/public information aggregator 708 aggregates, organizes, formats, and attaches metadata to data acquired via public data sharing network 702, interpersonal data sharing network 704, and intrapersonal data sharing network 706. The resultant aggregate is fed into the raw data queue 710 of a recording subsystem, such as recording subsystem 500 in FIG. 5.

Figure 8:
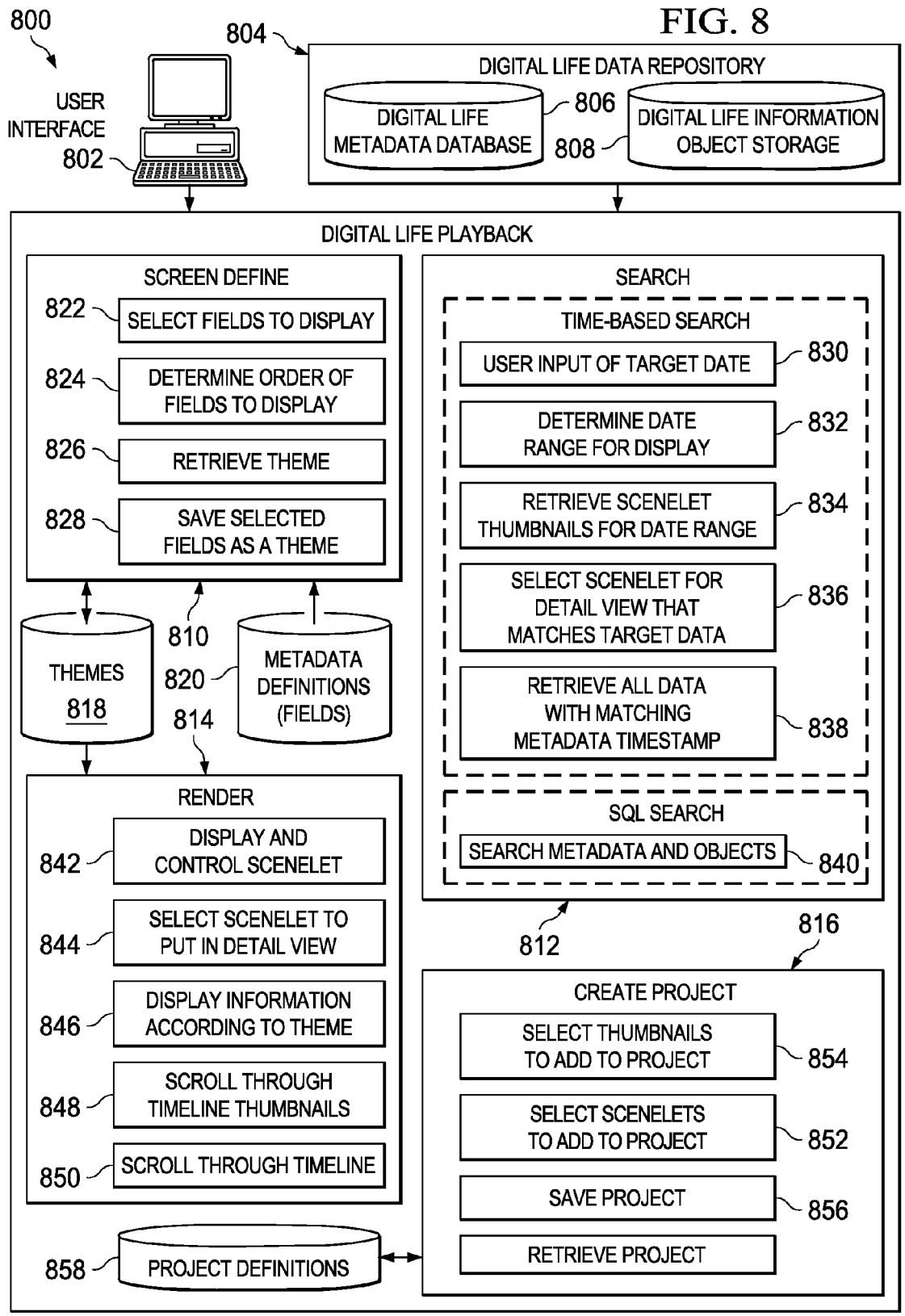
FIG. 8 is a block diagram illustrating the components of a playback subsystem in accordance with an illustrative embodiment.

FIG. 8 is a block diagram illustrating the components of a playback subsystem in accordance with an illustrative embodiment. The components of playback subsystem 800 illustrated in FIG. 8 may be implemented in a data processing system, such as data processing system 200 as shown in FIG. 2.

In this example, playback subsystem 800 comprises of several subsystems, such as, but not limited to, screen define subsystem 810, search subsystem 812, render subsystem 814, and create project subsystem 816. Additionally, playback subsystem 800 includes a user interface 802 associated with the digital life recording system. User interface 802 may be used to organize and present information stored in a data repository, such as repository database 608 shown in FIG. 6.

Playback subsystem 800 interfaces with digital life data repository 804. Digital life data repository 804 includes digital life metadata database 806 and digital life information object storage database 808. Digital life data repository 804 may be similarly implemented as repository database 608 shown in FIG. 6.

Screen define subsystem 810 provides an interface to receive user inputs, such as, but not limited to, selecting the type of information a user wants to view. The type of information may include, but is not limited to, video information, sound information, temperature sensor information, or any of the other information captured by the recording system or network data sharing system. The definition for these types of information and their mapping to the digital life data database is managed through metadata definitions database 820. The information can be organized on user interface 802 and then saved in themes database 818 using the function save selected fields as a theme (block 828). Saved themes may be retrieved from themes database 818 using the retrieve theme (block 826) functionality. Other functionality provided by screen define subsystem 810 may include, but is not limited to, computer-usable program code that allows a user to select fields to display (block 822), and to determine order of fields to display (block 824).

Search subsystem 812 allows a user to input a date/time range to select the data that the user wants to view (block 830). Search subsystem 812 determines the initial date range to display on the user interface (block 832) prior to searching digital life data repository 804. Search subsystem 812 retrieves the scenelet thumbnails from digital life information object storage database 808 for the time slices within the date range (block 834). A scenelet is a snippet of a scene. Additional details about a selected scenelet may be viewed (block 836).

For all non-video information or metadata that is to be displayed on the screen, such as, but not limited to, sound and temperature, similar searching is performed and summaries retrieved for each time slice (block 838). Detailed information for the requested date/time will also be retrieved. Similarly, a generic searching capability is provided that uses standard search language queries, such as Structured Query Language (SQL), to allow access to any aspect of digital life data repository 804 (block 840).

Render subsystem 814 is used to render the information retrieved, using search subsystem 812, on user interface 802. As stated above, the layout of user interface 802 is defined using screen define subsystem 810 and stored in themes database 818. Render subsystem 814 provides functionality to display, manipulate, and control a scenelet (block 842), select a scenelet for a detail view (block 844), display information according to theme (block 846), scroll through time line of thumbnails (block 848), and scroll through time line (block 850).

Create project subsystem 816 is used to support the creation of a saved set of information found in digital life data repository 804. A user may, using user interface 802, select either scenelets (block 852) or thumbnails (block 854), from the render subsystem 814 and save the group of items as a project (block 856) in a project definitions database 858. Additionally, previously saved projects may be retrieved from the project definitions database 858 using user interface 802.

Figure 9:
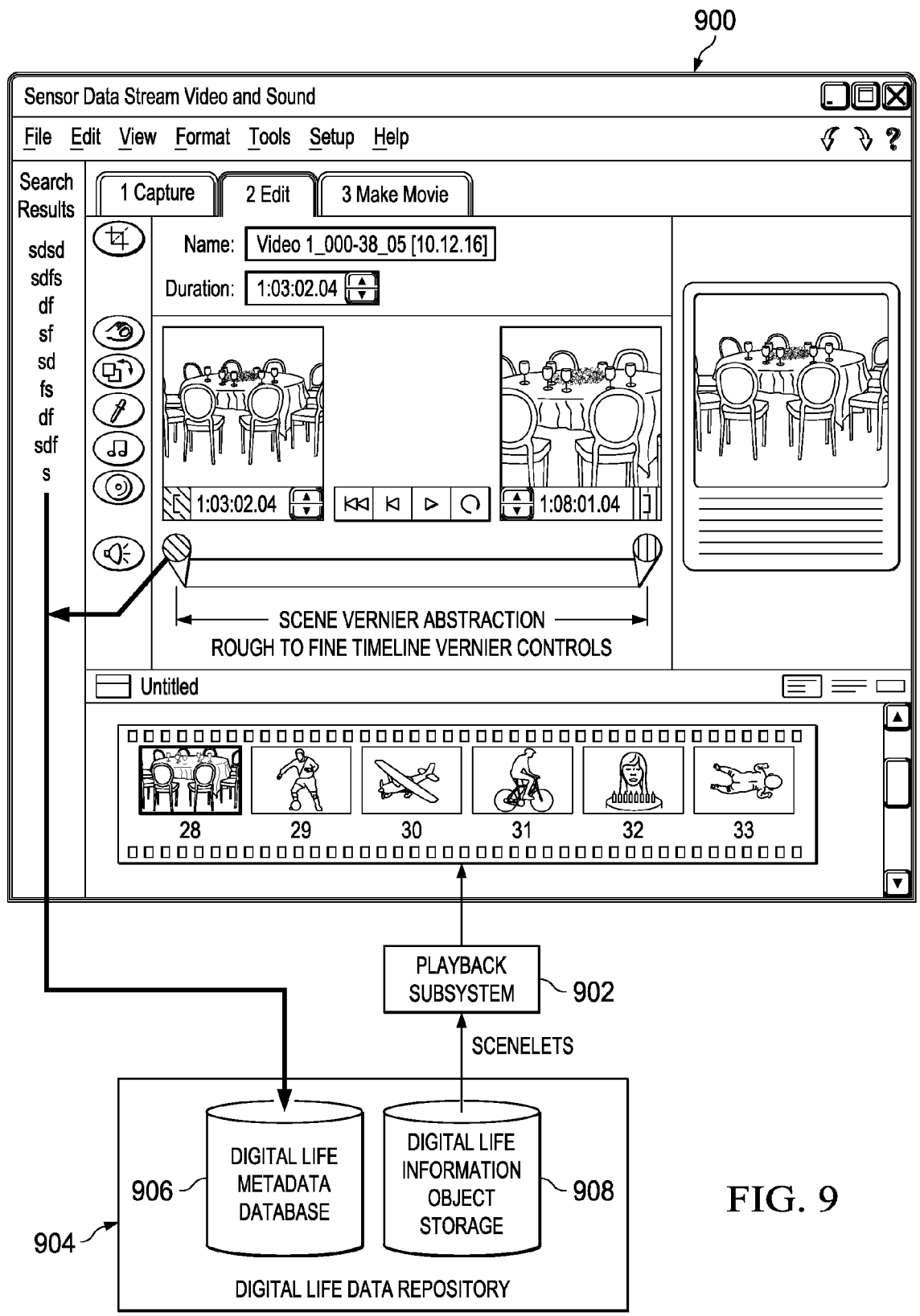
FIG. 9 is a diagram depicting a user interface associated with the playback subsystem in accordance with an illustrative embodiment.

FIG. 9 is a diagram depicting a user interface associated with the playback subsystem in accordance with an illustrative embodiment. Playback subsystem 902 uses data acquired from a digital life data repository 904. Digital life data repository 904 contains digital life metadata database 906 and digital life information object storage database 908. Digital life data repository 904 may be similarly implemented as repository database 608 shown in FIG. 6.

The results associated with a search are depicted on the left hand side of user interface 900. Additionally, user interface 900 provides a mechanism for adjusting the timeline vernier. The timeline vernier controls the precision of time. Thus, a user can adjust from a rough timeline vernier to a more precise/fine timeline vernier. Scenelets associated with a selected result is presented in the bottom half of user interface 900.

Figure 10:
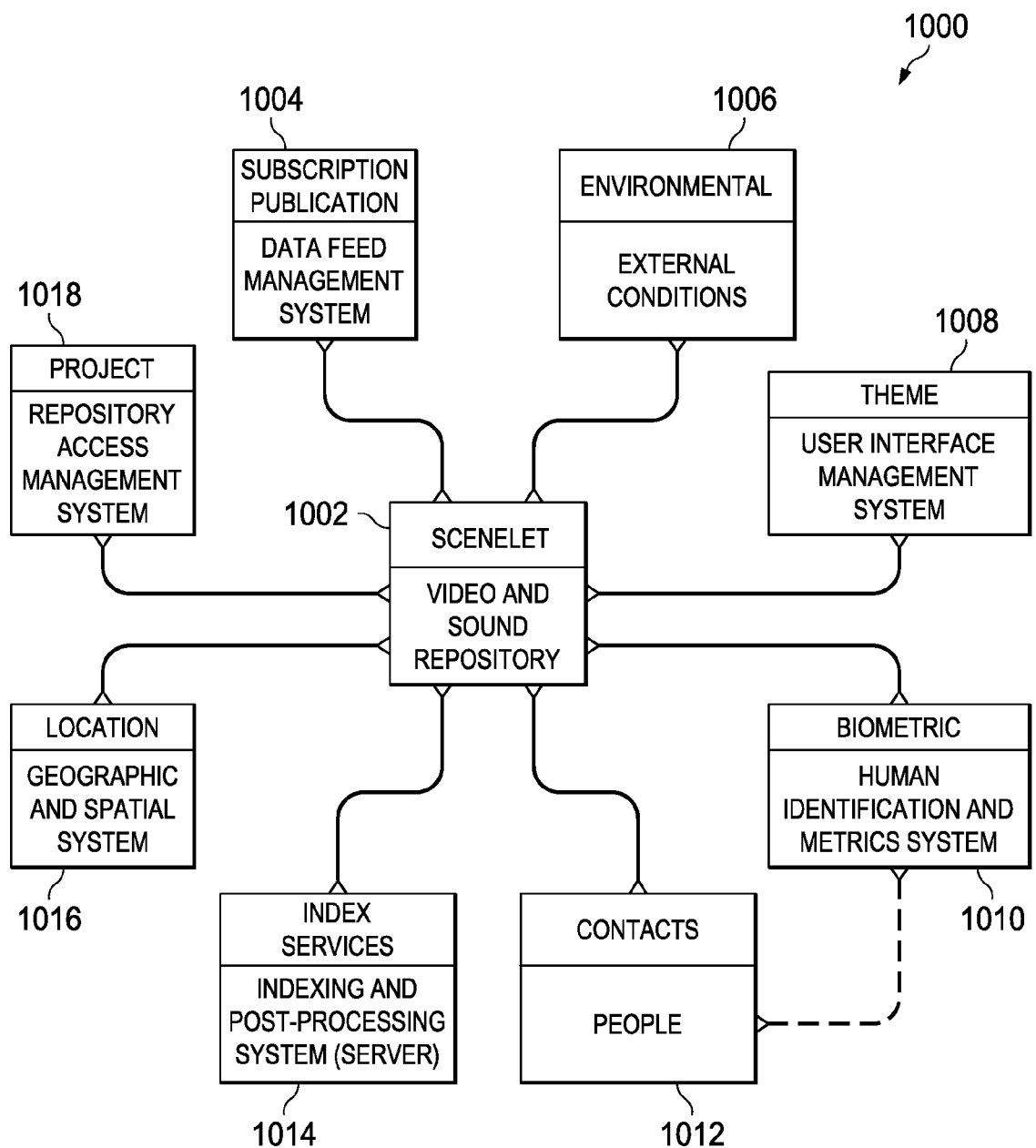
FIG. 10 is a diagram depicting a data model in accordance with an illustrative embodiment.

FIG. 10 is a diagram depicting a data model in accordance with an illustrative embodiment. Digital life conceptual data model 1000 may include, but is not limited to, the following subsystems: scenelet 1002, subscription/publication 1004, environmental 1006, theme 1008, biometric 1010, contacts 1012, index services 1014, location 1016, and project 1018.

Scenelet 1002 organizes and manages the image and sound files. Subscription/publication 1004 manages the external data feeds into and out of the digital life system, such as digital life recording system 300 shown in FIG. 3. Environmental 1006 captures and manages environmental characteristics related to the scenelet data. Theme 1008 allows users to customize and manage their digital life system interfaces and experiences. Biometric 1010 captures and manages biometric information associated with human contacts within the scenelets. Contacts 1012 is a repository of known contacts. Index services 1014 provides post processing capability to further analyze and categorize scenelet data. Location 1016 captures and manages specific location related details during a scenelet. Project 1018 provides an access management system that allows users to customize data retrieval.

Figure 11:
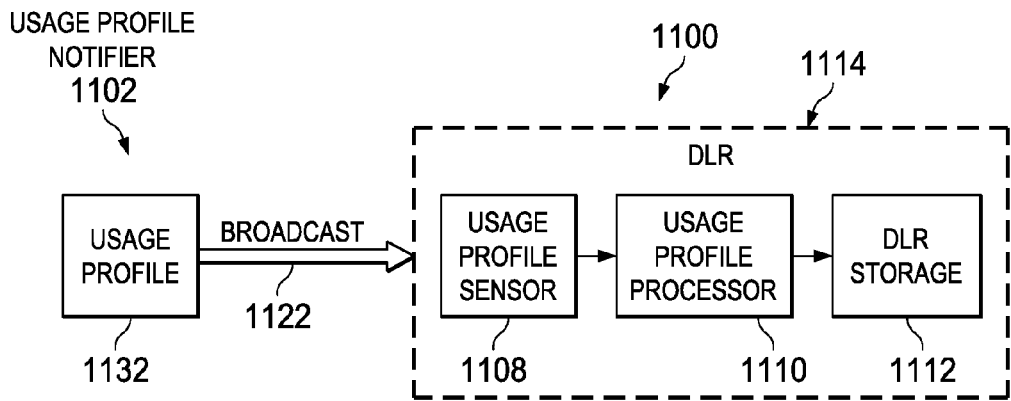
FIG. 11 is a block diagram showing an implementation of a digital life recorder subsystem configured for use with a usage profile environment in accordance with an illustrative embodiment.

FIG. 11 is a block diagram showing an implementation of a digital life recorder subsystem configured for use with a usage profile environment in accordance with an illustrative embodiment. In this example, usage profile environment 1100 comprises digital life recording subsystem 1114, usage profile notifier 1102, and broadcast 1122. Digital life recording subsystem 1114 comprises of usage profile sensor 1108, usage profile processor 1110, and digital life recorder storage 1112. Digital life recording subsystem 1114 may be implemented as digital life recording subsystem 304 as shown in FIG. 3. Usage profile sensor 1108 and usage profile processor 1110 may be implemented in a recording subsystem, such as recording subsystem 116 as shown in FIG. 1. Digital life recorder storage 1112 may be implemented in a digital life repository subsystem, such as digital life repository subsystem 306 as shown in FIG. 3. Digital life recording subsystem 1114 may be implemented in a data processing system, such as data processing system 200 as shown in FIG. 2 and client 110 as shown in FIG. 1.

While a digital life recorder, such as digital life recorder 300 as shown in FIG. 3, captures data, usage profile sensor 1108 can monitor for usage profile broadcast 1122 from usage profile notifier 1102. Usage profile sensor 1108 captures data that defines a usage profile, such as usage profile 1132. Once data is captured by usage profile sensor 1108, the data is sent to usage profile processor 1110.

Usage profile processor 1110 may be implemented as a processor, such as processor unit 204 as shown in FIG. 2. Usage profile processor 1110 can take the usage profile 1132 and associate usage profile 1132 with the current date and time as the start time. Then, usage profile processor 1110 continues to monitor the input from the usage profile sensor 1108 until the digital life recorder 300 moves out of range or view of usage profile broadcast 1122 that the usage profile processor 1110 is monitoring. Once digital life recorder 300 moves out of range, usage profile processor 1110 associates the current date and time as the end time and then submits usage profile 1132, the start time, and the end time to digital life recorder storage 1112 for later use.

Usage profile 1132 can comprise a usage policy. A usage policy can be, for example, a policy that contains information on how a person wants his/her image and conversations being used. Also, for example, the usage policy can be a policy that contains information on how a building or location wants to restrict how recordings in the building or location can be used. Also, for example, the usage policy can be a policy that contains information on how a content provider, such as a concert or class, wants to restrict the content from being rebroadcast.

Figure 12:
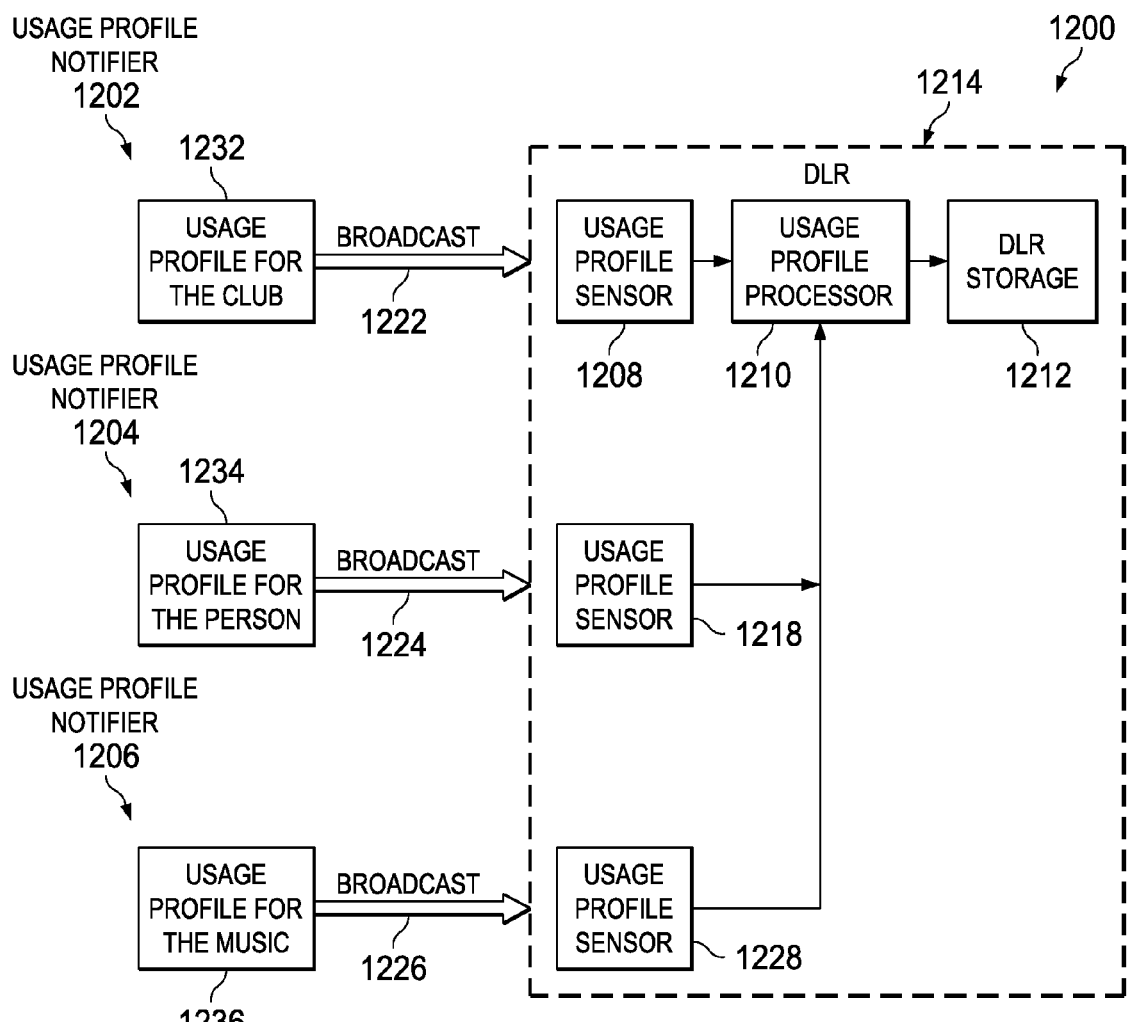
FIG. 12 is a block diagram showing an implementation of a digital life recorder subsystem configured for use with a usage profile environment with multiple usage profiles and multiple usage profile sensors in accordance with an illustrative embodiment.

FIG. 12 is a block diagram showing an implementation of a digital life recorder subsystem configured for use with a usage profile environment with multiple usage profiles and multiple usage profile sensors in accordance with an illustrative embodiment. In this example, usage profile environment 1200 comprises digital life recording subsystem 1214, usage profile notifiers 1202, 1204, and 1206, and broadcasts 1222, 1224, and 1226. Digital life recording subsystem 1214 comprises of usage profile sensors 1208, 1218, and 1228, usage profile processor 1210, and digital life recorder storage 1212. Digital life recording subsystem 1214 may be implemented as digital life recording subsystem 304 as shown in FIG. 3. Usage profile sensors 1208, 1218, and 1228 and usage profile processor 1210 may be implemented in a recording subsystem, such as recording subsystem 116 as shown in FIG. 1. Digital life recorder storage 1212 may be implemented in a digital life repository subsystem, such as digital life repository subsystem 306 as shown in FIG. 3. Digital life recording subsystem 1214 may be implemented in a data processing system, such as data processing system 200 as shown in FIG. 2 and client 110 as shown in FIG. 1.

Usage profile sensors 1208, 1218, and 1228 can each capture multiple usage profile broadcasts 1222, 1224, and 1226 simultaneously. This would be useful, for example, at a concert. A user is recording content in a club. The user could be receiving a broadcast from the club itself with a usage profile 1232 for the images of the club, a usage profile 1234 from a person on a dance floor for the images of the person, and usage profile 1236 for music from a live band for the music the band produces. The usage profile sensor 1208 can pass all of its information to the usage profile processor 1210. In any embodiment there may be one or more than one usage profile sensors. The usage profile processor 1210 can track each profile individually.

Figure 13:
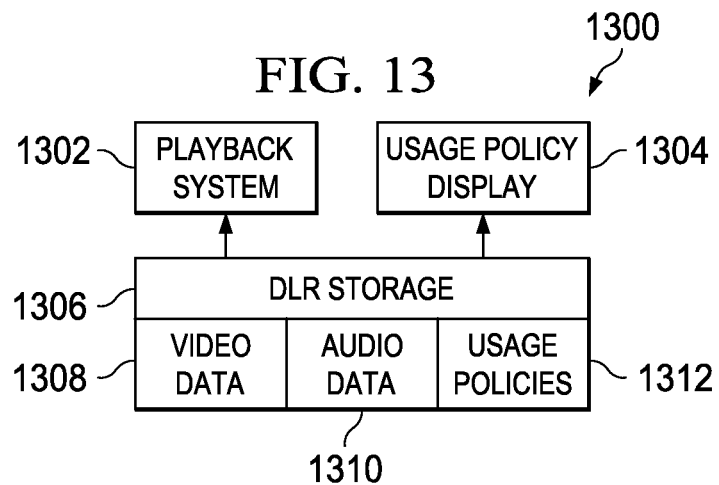
FIG. 13 is a block diagram showing an implementation of a playback subsystem configured for use with a usage profile playback system in accordance with an illustrative embodiment.

FIG. 13 is a block diagram showing an implementation of a playback subsystem configured for use with a usage profile playback system in accordance with an illustrative embodiment. In this example, usage profile playback system 1300 comprises playback system 1302, usage policy display 1304, and digital life recorder storage 1306. Digital life recorder storage 1306 comprises of video data 1308, audio data 1310, and usage policies 1312. Digital life recorder storage 1306 may be implemented in a digital life repository subsystem, such as digital life repository subsystem 306 as shown in FIG. 3 or digital life data repository 804 as shown in FIG. 8. Usage profile playback system 1300 may be implemented in a data processing system, such as data processing system 200 as shown in FIG. 2 and client 110 as shown in FIG. 1. Playback system 1302 may be implemented in a playback subsystem such as playback subsystem 800 as shown in FIG. 8. Playback system 1302 may be displayed on a display such as user interface 802 as shown in FIG. 8.

Playback system 1302 displays video data 1308 and audio data 1310. Usage policy display 1304 displays usage policies 1312. The usage policies 1312 displayed by usage policy display 1304 are associated with the video data 1308 and audio data 1310 displayed by playback system 1302.

Figure 14:
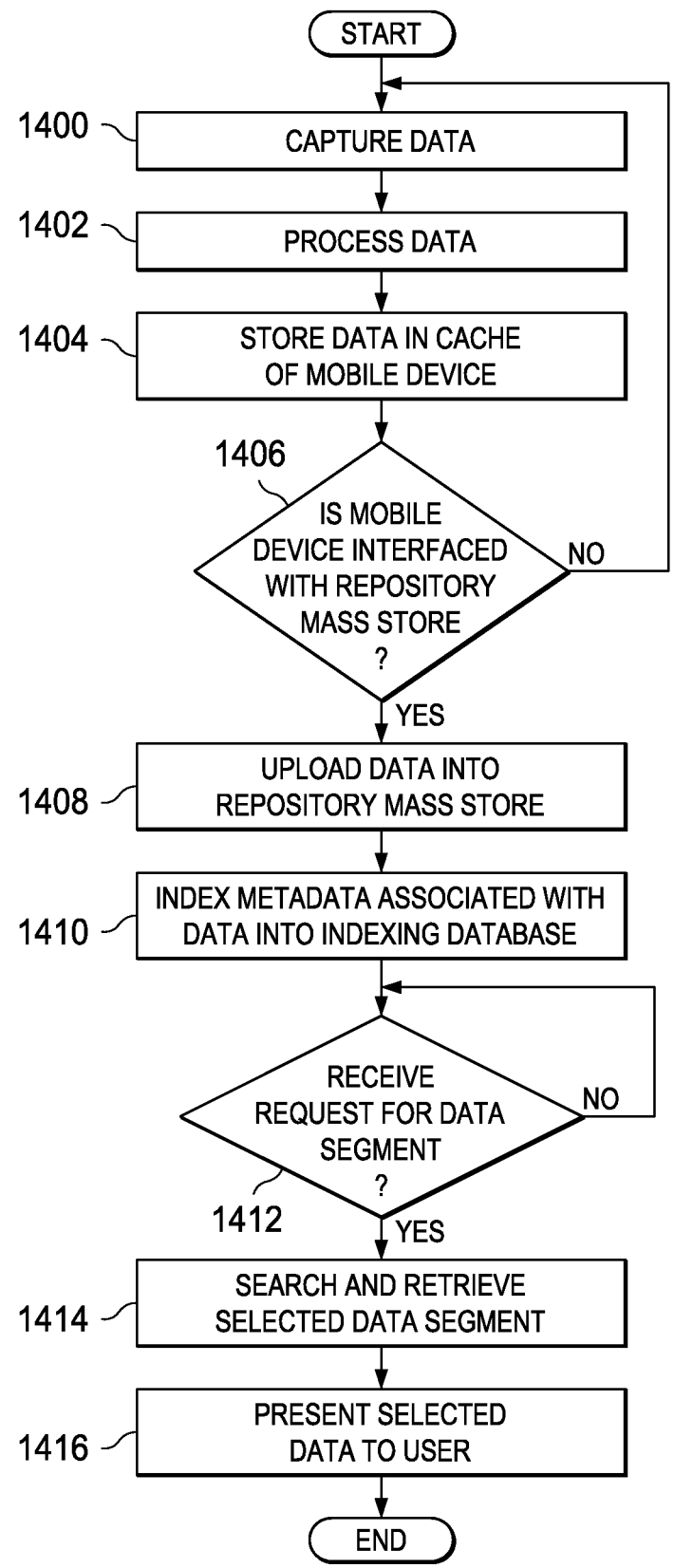
FIG. 14 is a high-level flowchart illustrating a process for capturing, storing, and presenting data in accordance with an illustrative embodiment.

FIG. 14 is a high-level flowchart illustrating a process for capturing, storing, and presenting data in accordance with an illustrative embodiment. The process illustrated in FIG. 14 may be implemented in a digital life recording system, such as digital life recording system 300 shown in FIG. 3.

The process begins by capturing data associated with daily activities of a person using data capturing devices (step 1400). The captured data is processed by a mobile device associated with the person (step 1402). The data is then stored in a cache of the mobile device (step 1404). The process monitors the mobile device to determine when the mobile device is interfaced with a repository mass store (step 1406). Interfacing may occur when the mobile device is in the vicinity of the repository mass store and connection is established via a wireless transmission link. Interfacing may also occur when the mobile device is docked to a repository mass store. The process continues the process of capturing (step 1400), processing (step 1402), and storing (step 1404) the data until a determination is made that the mobile device is interfaced with a repository mass store.

In response to interfacing the mobile device to a repository mass store, the process uploads the data stored in the cache of the mobile device into the repository mass store (step 1408). Metadata associated with the data, is indexed into an indexing database (step 1410). The process monitors for a request, from a user, to retrieve a selected data segment (step 1412). In response to receiving a request for a selected data segment, the process performs a search and retrieves the selected data segment from the repository mass store (step 1414). The process presents the selected data segment to the user (step 1416), with the process terminating thereafter.

Figure 15:
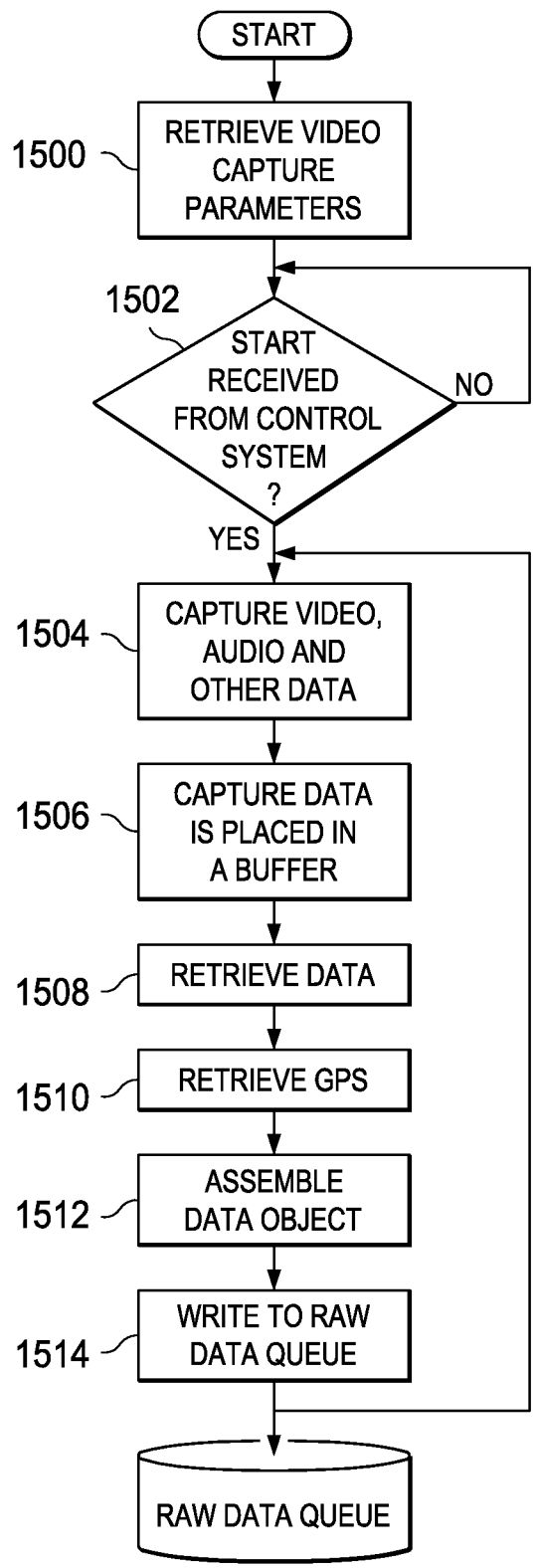
FIG. 15 is a flowchart of a process for capturing life data in accordance with an illustrative embodiment.

FIG. 15 is a flowchart illustrating a process for capturing life data in accordance with an illustrative embodiment. The process illustrated in FIG. 15 may be implemented in a digital life recording system, such as digital life recording system 300 shown in FIG. 3.

The process begins by retrieving the video capture parameters (step 1500). The process monitors for start request from the control system (step 1502). In response to receiving a start request from the control system, the process captures the video, audio, and other data from the data capturing devices associated with a person (step 1504). The captured data is placed in a buffer for temporary storage (step 1506). The process retrieves data from the buffer (step 1508). Additionally, the process retrieves data associated with a global positioning system device (step 1510). The process assembles a data object by associating the data associated with a global positioning system device with the data retrieved from the buffer (step 1512). The process writes the data object to a raw data queue (step 1514). The process repeats steps 1504-1514 until all the data in the buffer is written to the raw data queue.

Figure 16:
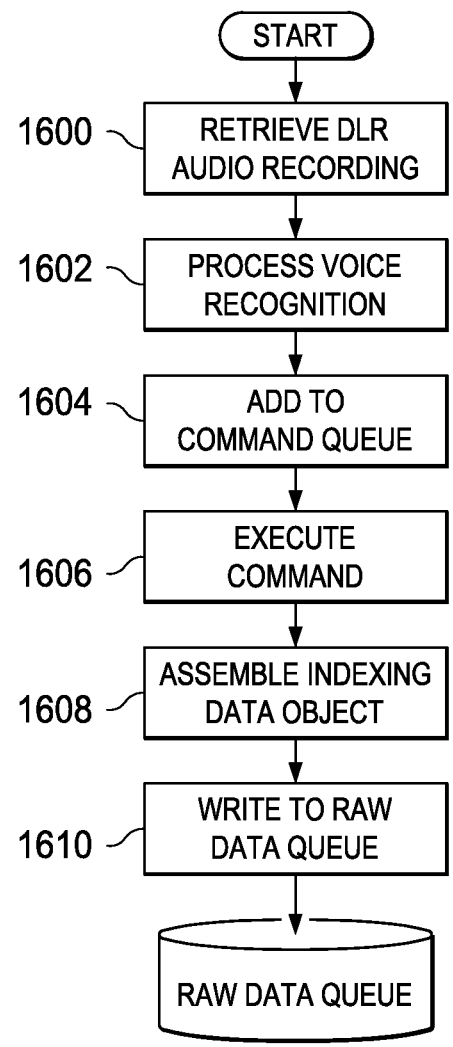
FIG. 16 is a flowchart of a process for improving the indexing of the stored data by tagging life data objects in accordance with an illustrative embodiment.

FIG. 16 is a flowchart of a process for improving the indexing of the stored data by tagging life data objects in accordance with an illustrative embodiment. The process illustrated in FIG. 16 may be implemented in a digital life recording system, such as digital life recording system 300 shown in FIG. 3.

The process begins by retrieving audio recording associated with a digital life recording system (step 1600). The audio recording is processed through a voice recognition subsystem to interpret voice commands (step 1602). The process adds the voice commands to a command queue (step 1604). Commands may also be added to the command queue using a mouse or keyboard. The tagging command includes a timestamp and a descriptive text index tag string. The process executes the commands stored in the command queue (step 1606). The process assembles the descriptive text index tag string and timestamp into an indexing data object (step 1608). The process writes the tagged data object to a raw data queue (step 1610) for later placement into the metadata database, with the process terminating thereafter.

Figure 17:
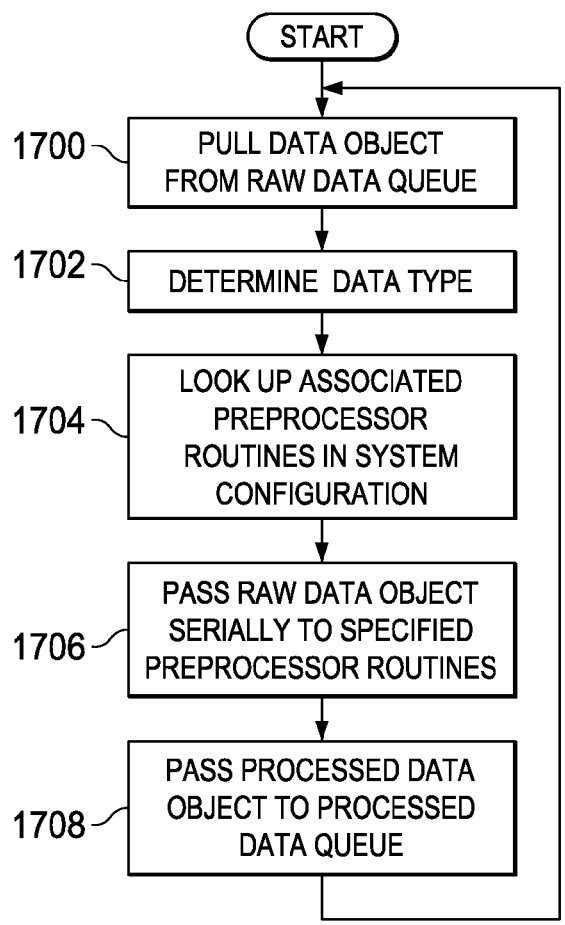
FIG. 17 is a flowchart of a process for preprocessing raw recorded data in accordance with an illustrative embodiment.

FIG. 17 is a flowchart illustrating a process for preprocessing raw recorded data in accordance with an illustrative embodiment. The process illustrated in FIG. 17 may be implemented in a digital life recording system, such as digital life recording system 300 shown in FIG. 3.

The process begins by pulling a data object from the raw data queue (step 1700). The process determines the data type of pulled data object (step 1702). The process looks up the associated preprocessor routines in system configuration (step 1704). The process passes the raw data object serially to the specified preprocessor routines (step 1706). The specified preprocessor routines return the processed data object to the process. The process then passes the processed data object to a processed data queue (step 1708). The process loops and repeats steps 1700-1708.

Figure 18:
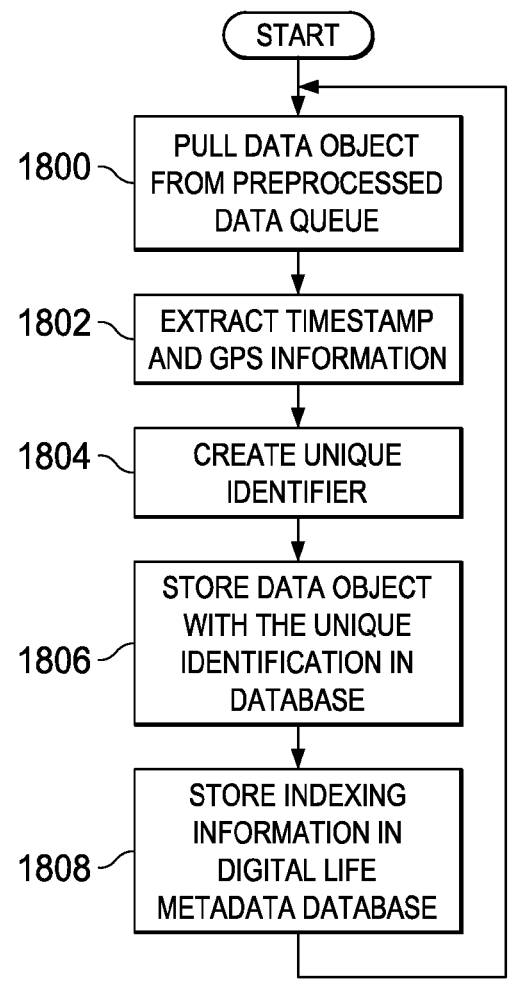
FIG. 18 is a flowchart of a process for creating a unique identifier for indexing and storing data objects in accordance with an illustrative embodiment.

FIG. 18 is a flowchart of a process for creating a unique identifier for indexing and storing data objects in accordance with an illustrative embodiment. The process illustrated in FIG. 18 may be implemented in a digital life recording system, such as digital life recording system 300 shown in FIG. 3.

The process begins by pulling a data object from the preprocessed data queue (step 1800). The process extracts the timestamp and global positioning system (GPS) information from the data object (step 1802). The process creates a unique identifier for identifying the data object (step 1804). The process then stores the data object along with the unique identifier in a digital life information object storage database (step 1806), such as digital life repository information object storage 630 shown in FIG. 6. The process stores indexing information, such as, but not limited to, a timestamp, global positioning system information, the unique identifier, and the physical location of where the data object is stored in the digital life information object storage database, in a digital life repository metadata database (step 1808), such as digital life repository metadata database 628 shown in FIG. 6. The process loops and repeats steps 1800-1808.

Figure 19:
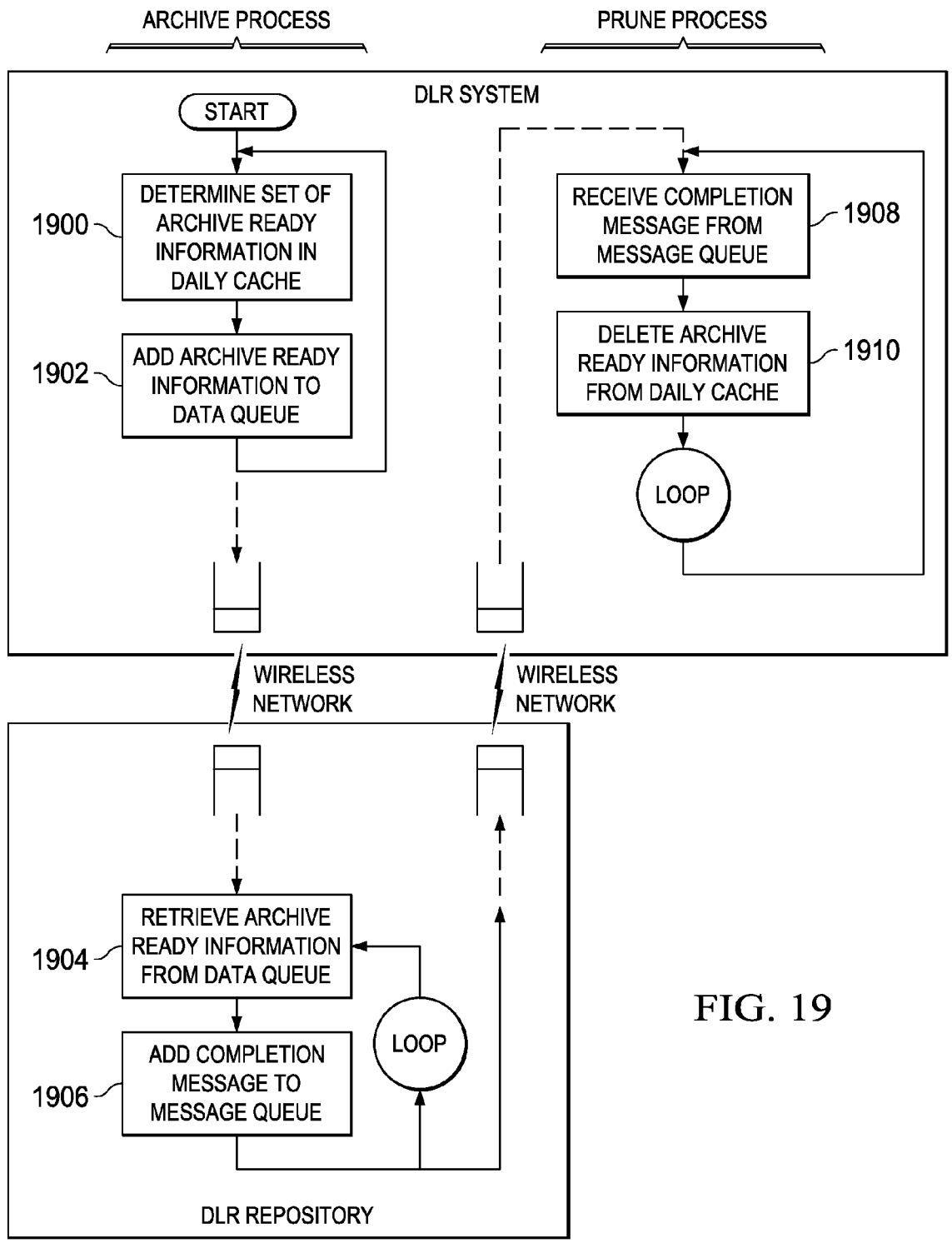
FIG. 19 is a flowchart of a process for archiving data objects in accordance with an illustrative embodiment.

FIG. 19 is a flowchart of a process for archiving data objects in accordance with an illustrative embodiment. The process illustrated in FIG. 19 may be implemented in a digital life recording system, such as digital life recording system 300 shown in FIG. 3.

The process begins by determining a set of archive ready information stored in the daily cache of a mobile device (DLR system) (step 1900). The mobile device is associated with a person being recorded. The archive ready information comprises of the stored data objects, metadata, and other data associated with the captured data. The process adds the set of archive ready information to a data queue (step 1902). The process loops and repeats the steps of determining (step 1900) and adding (step 1902) archive ready information to a data queue until there is no more archive ready information.

In response to the mobile device interfacing with a repository mass store, the process retrieves the set of archive ready information from the data queue (step 1904). The process inserts the set of archive ready information into the repository mass store, such as repository database 608 shown in FIG. 6. The process then adds a completion message to a message queue (step 1906). The process loops and repeats the steps of retrieving (step 1904) and inserting (step 1906) archive ready information into the repository mass store until all archive ready information is stored in the repository mass store.

The process receives completion messages from the message queue (step 1908). In response to receiving the completion messages from the message queue, the process deletes the set of archive ready information from the daily cache (step 1910). The process loops and repeats the steps of receiving completion messages from the message queue (step 1908) and deleting the set of archive ready information from the daily cache (step 1910).

Figure 20:
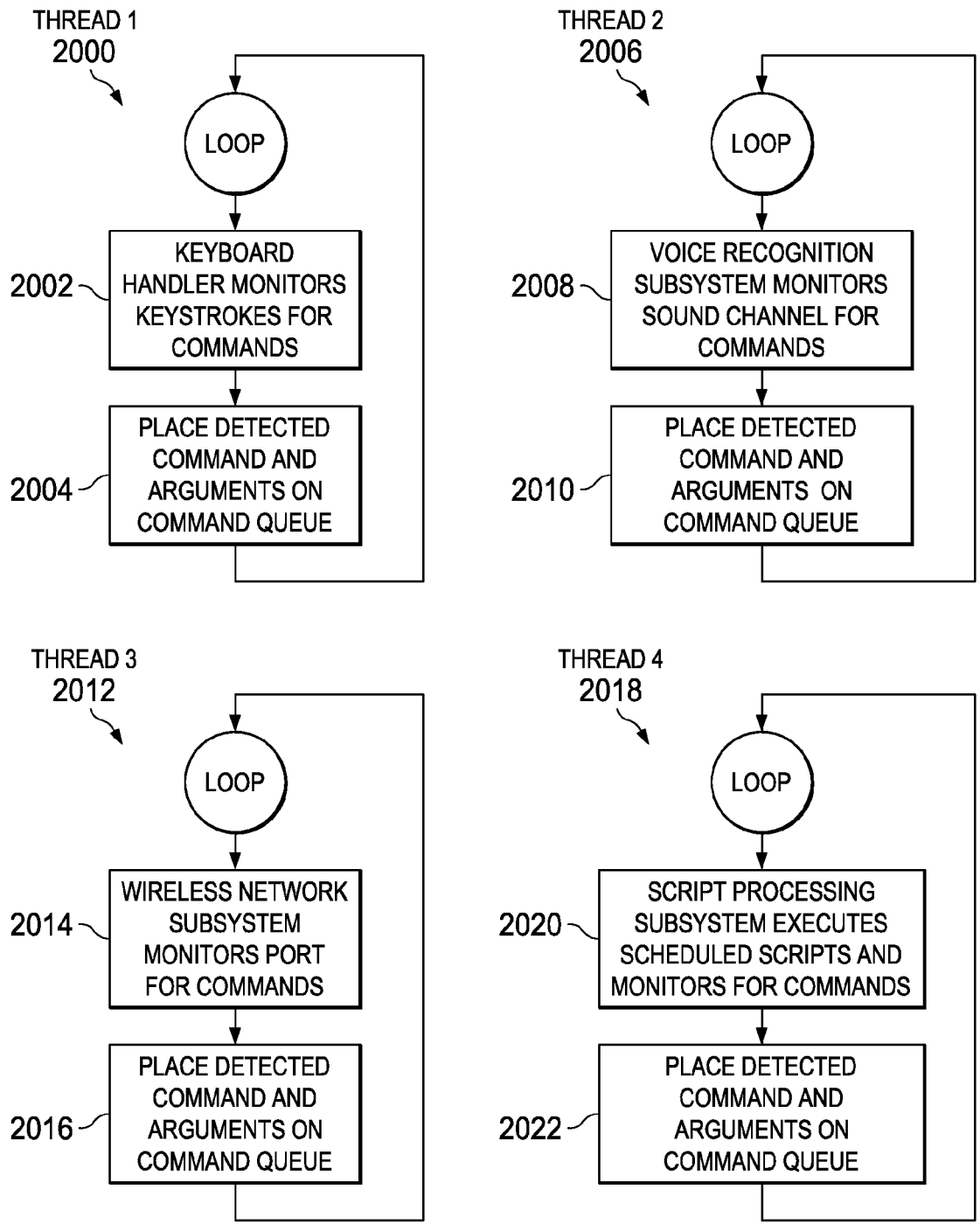
FIG. 20 illustrates different processes for adding commands to a command queue in accordance with an illustrative embodiment.

FIG. 20 illustrates different processes for adding commands to a command queue in accordance with an illustrative embodiment. The processes illustrated in FIG. 20 may be implemented in a digital life recording system, such as digital life recording system 300 shown in FIG. 3.

In process 2000, a keyboard handler monitors keystrokes for commands (step 2002). In response to detecting a command, the detected command along with the associated arguments is placed on the command queue (step 2004). Process 2000 loops and continues monitoring (step 2002) and adding detected commands (step 2004) to the command queue.

In process 2006, a voice recognition subsystem monitors the sound channels for commands (step 2008). In response to detecting a command, the detected command along with the associated arguments is placed on the command queue (step 2010). Process 2006 loops and continues monitoring (step 2008) and adding detected commands (step 2010) to the command queue.

In process 2012, a wireless network subsystem monitors the ports for commands (step 2014). In response to detecting a command, the detected command along with the associated arguments is placed on the command queue (step 2016). Process 2012 loops and continues monitoring (step 2014) and adding detected commands (step 2016) to the command queue.

In process 2018, a script processing subsystem executes scheduled scripts and monitors for commands (step 2020). In response to detecting a command, the detected command along with the associated arguments is placed on the command queue (step 2022). Process 2018 loops and continues monitoring (step 2020) and adding detected commands (step 2022) to the command queue.

Figure 21:
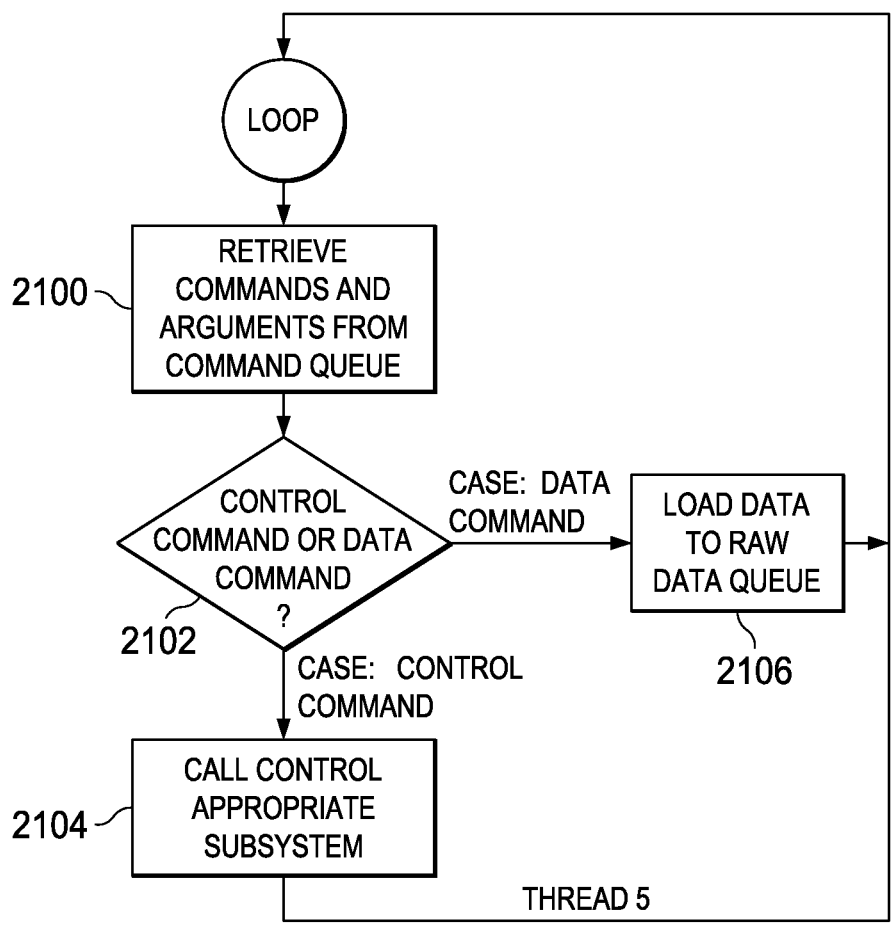
FIG. 21 is a flowchart of a process for processing commands is depicted in accordance with an illustrative embodiment.

FIG. 21 is a flowchart of a process for processing commands in accordance with an illustrative embodiment. The process illustrated in FIG. 21 may be implemented in a digital life recording system, such as digital life recording system 300 shown in FIG. 3.

The process begins by retrieving commands and their associated arguments from a command queue (step 2100), such as command queue 512 shown in FIG. 5. The process interprets the retrieved command to determine if the retrieved command is a control command or a data command (step 2102). A control command is a command that modifies the operation of the digital life recording system. A data command is command request to select data associated with the digital life recording system.

In response to determining that the retrieved command is a control command, the process calls the control appropriate subsystem for processing the command (step 2104). In response to determining that the retrieved command is a data command, the process loads selected data to the raw data queue (step 2106). The process loops and repeats steps 2100-2106 for all commands in the command queue.

Figure 22:
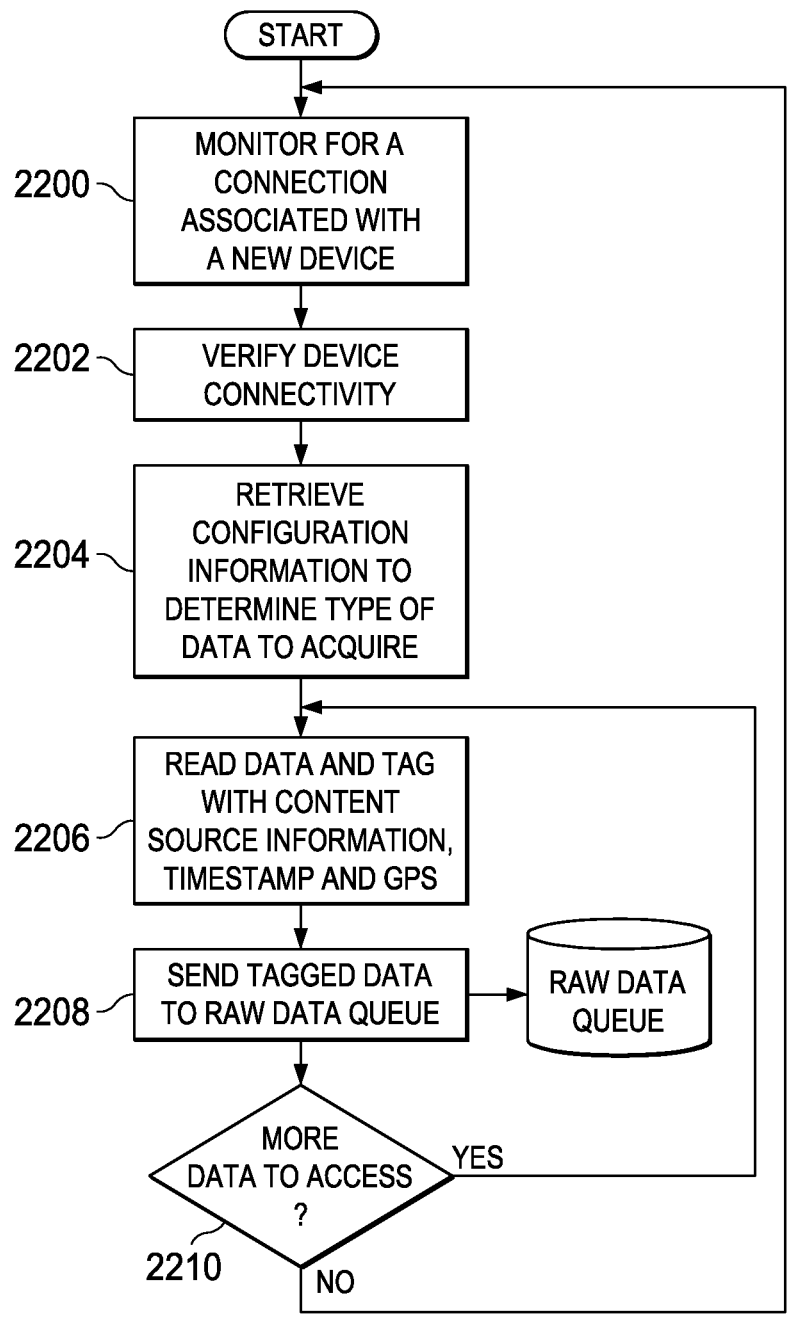
FIG. 22 is a flowchart of a process for acquiring and organizing personal device data is depicted in accordance with an illustrative embodiment.

FIG. 22 is a flowchart of a process for acquiring and organizing personal device data in accordance with an illustrative embodiment. The process illustrated in FIG. 22 may be implemented in a digital life recording system, such as digital life recording system 300 shown in FIG. 3.

The process begins by monitoring for a connection associated with a new device (step 2200). The connection may be established either wirelessly, such as, but not limited to, Bluetooth enabled devices, or the connection may be established through a physical connection, such as, but not limited to, universal serial bus (USB) devices. The devices may include, but are not limited to, cellular phones, personal digital assistants (PDAs), and digital cameras. Responsive to detecting a connection, the process verifies the device connectivity (step 2202).

The process retrieves configuration information to determine the type of data to acquire from the connected device (step 2204). The process then reads data from the connected device(s) and tags the data with the content source information, a timestamp and global positioning system location (step 2206). The process sends the tagged data to the raw data queue (step 2208). The process determines whether more data exists in the connected device (step 2210). In response to a determination that more data exists in the connected device, the process repeats the steps of reading and tagging the data (step 2206), and sending the tagged data to the raw data queue (step 2208). In response to a determination that more data does not exist in the connected device, the process returns to the step of monitoring for a connection associated with a new device (step 2200).

Figure 23:
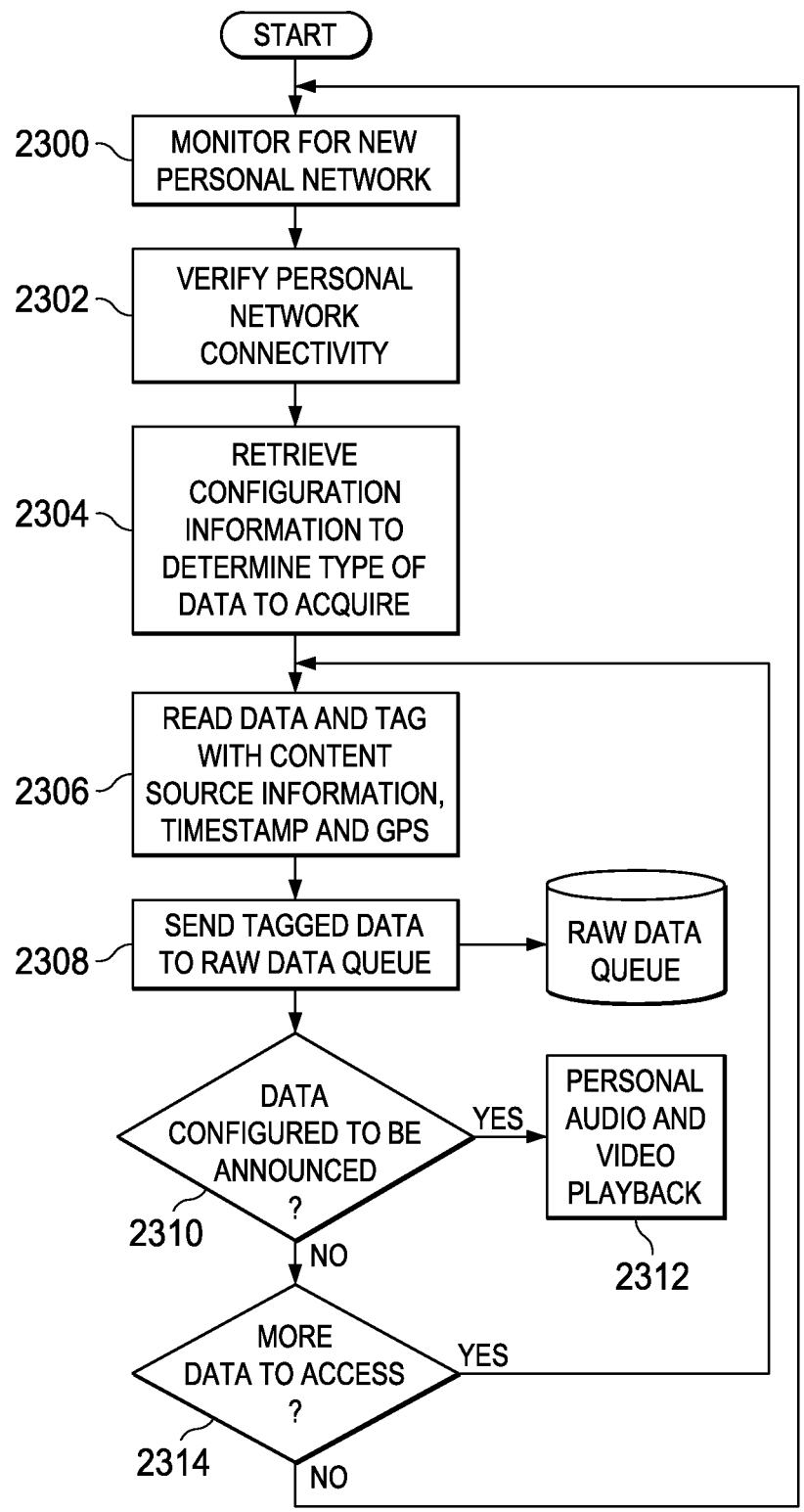
FIG. 23 is a flowchart of a process for acquiring and organizing personal network data in accordance with an illustrative embodiment.

FIG. 23 is a flowchart of a process for acquiring and organizing personal network data in accordance with an illustrative embodiment. The process illustrated in FIG. 23 may be implemented in a digital life recording system, such as digital life recording system 300 shown in FIG. 3.

The process begins by monitoring for a connection associated with a new personal network (step 2300). The connection may be established either by wired or wireless means. In response to detecting a connection, the process verifies the personal network connectivity (step 2302). The process retrieves configuration information to determine the type of data to acquire from the connected personal network (step 2304).

The process then reads data from the connected personal network and tags the data with the content source information, a timestamp and global positioning system location (step 2306). The process sends the tagged data to the raw data queue (step 2308).

The process determines whether the data is configured to be announced (step 2310). Responsive to a determination that the data is configured to be announced, the data is forwarded to a personal audio and video playback subsystem for announcing the data to the person (step 2312). The process determines whether more data exists in the connected personal network (step 2314).

In response to a determination that more data exists in the connected personal network, the process repeats the steps of reading and tagging the data (step 2306), sending the tagged data to the raw data queue (step 2308), and determining whether the data is configured to be announced (step 2310). In response to a determination that more data does not exist in the connected personal network, the process returns to the step of monitoring for a connection associated with a new personal network (step 2300).

Figure 24:
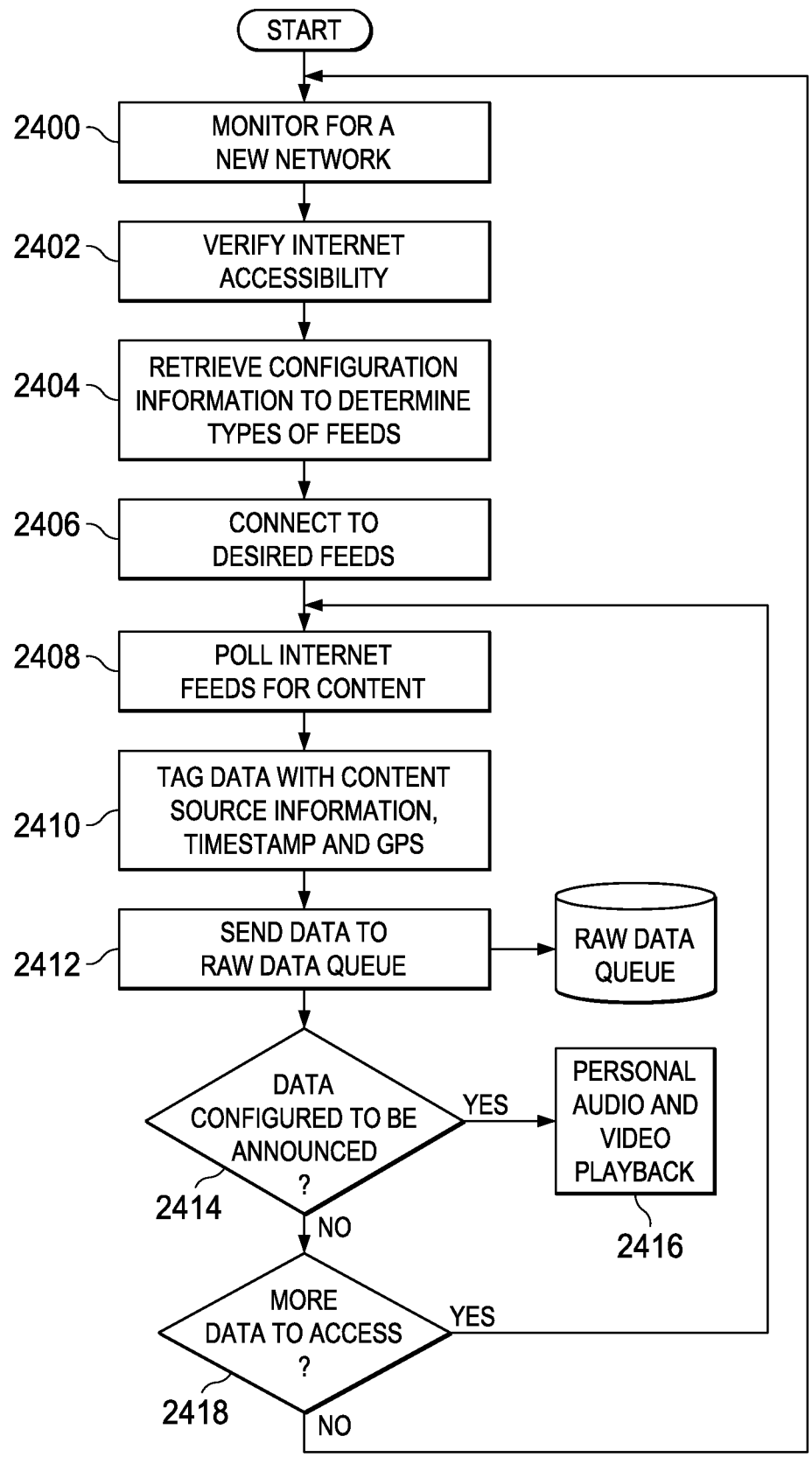
FIG. 24 is a flowchart of a process for acquiring and organizing data from the Internet in accordance with an illustrative embodiment.

FIG. 24 is a flowchart of a process for acquiring and organizing data from the Internet in accordance with an illustrative embodiment. The process illustrated in FIG. 24 may be implemented in a digital life recording system, such as digital life recording system 300 shown in FIG. 3.

The process begins by monitoring for a connection associated with a new network (step 2400). The connection may be established either by wired or wireless means. In response to detecting a connection, the process verifies internet accessibility (step 2402). The process then retrieves configuration information to determine the types of feeds to acquire (step 2404). A feed is data created by a party and broadcast over the internet to others. The process connects to the desired feeds (step 2406) and polls the internet feeds for content (step 2408). In response to receiving data/content from the internet feeds, the data is tagged with the content source information, a timestamp and global positioning system location (step 2410). The process sends the tagged data to the raw data queue (step 2412).

The process determines whether the data is configured to be announced (step 2414). Responsive to a determination that the data is configured to be announced, the data is forwarded to a personal audio and video playback subsystem for announcing the data to the person (step 2416). The process determines whether more data exists in the connected internet feeds (step 2418).

In response to a determination that more data exists in the connected internet feeds, the process repeats the steps of polling (step 2408) and tagging the data (step 2410), sending the tagged data to the raw data queue (step 2412), and determining whether the data is configured to be announced (step 2414). In response to a determination that more data does not exist in the connected internet feeds, the process returns to the step of monitoring for a connection associated with a new network (step 2400).

Figure 25:
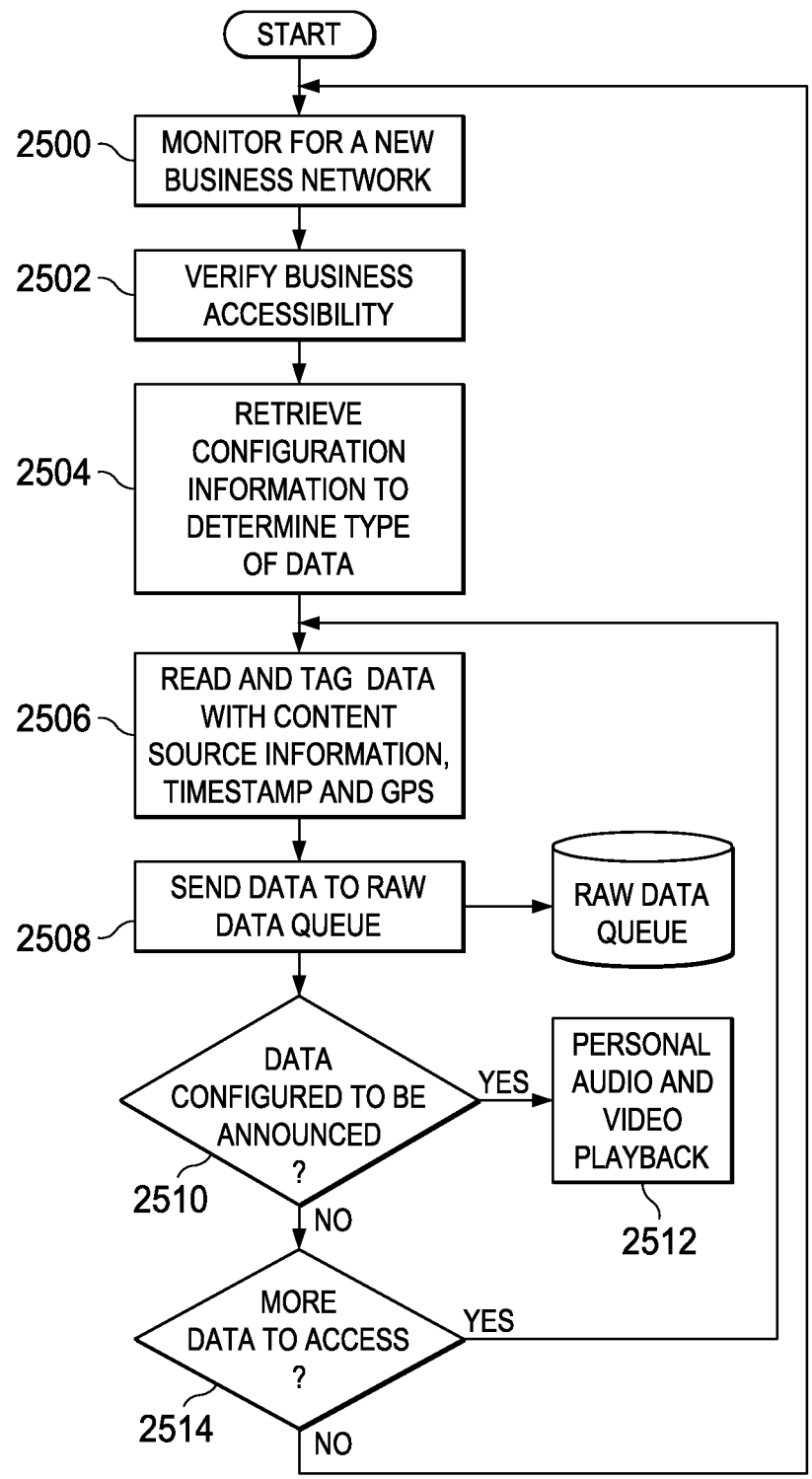
FIG. 25 is a flowchart of a process for acquiring and organizing data from business networks in accordance with an illustrative embodiment.

FIG. 25 is a flowchart of a process for acquiring and organizing data from business networks in accordance with an illustrative embodiment. The process illustrated in FIG. 25 may be implemented in a digital life recording system, such as digital life recording system 300 shown in FIG. 3.

The process begins by monitoring for a connection associated with a new business network (step 2500). The connection may be established either by wired or wireless means. In response to detecting a connection, the process verifies the business network connectivity (step 2502). The process retrieves configuration information to determine the type of data to acquire from the connected business network (step 2504). The process then reads data from the connected business network and tags the data with the content source information, a timestamp and global positioning system location (step 2506). The process sends the tagged data to the raw data queue (step 2508).

The process determines whether the data is configured to be announced (step 2510). Responsive to a determination that the data is configured to be announced, the data is forwarded to a personal audio and video playback subsystem for announcing the data to the person (step 2512). The process determines whether more data exists in the connected business network (step 2514).

In response to a determination that more data exists in the connected business network, the process repeats the steps of reading and tagging the data (step 2506), sending the tagged data to the raw data queue (step 2508), and determining whether the data is configured to be announced (step 2510). In response to a determination that more data does not exist in the connected business network, the process returns to the step of monitoring for a connection associated with a new business network (step 2500).

Figure 26:
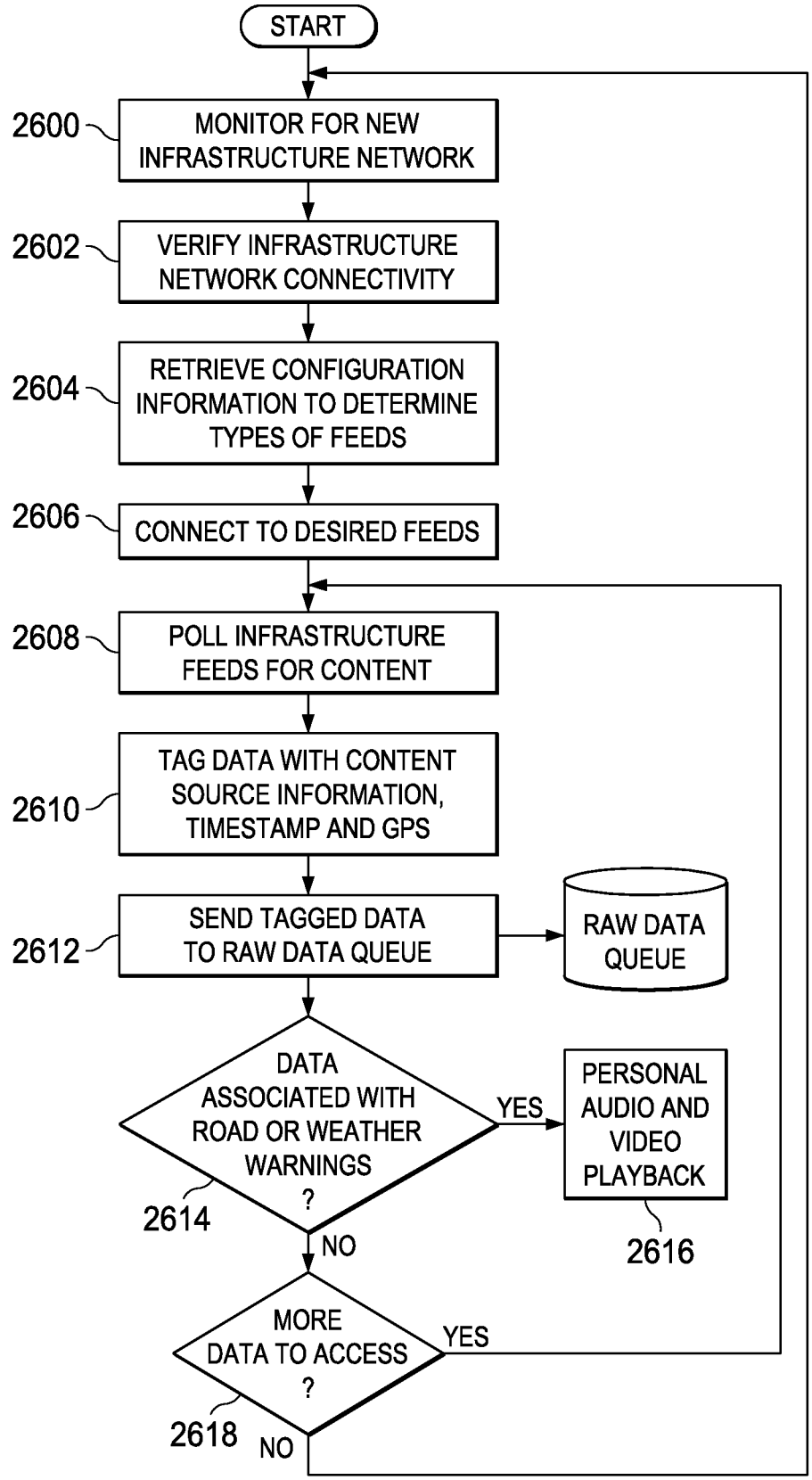
FIG. 26 is a flowchart of a process for acquiring and organizing data from infrastructure networks in accordance with an illustrative embodiment.

FIG. 26 is a flowchart of a process for acquiring and organizing data from infrastructure networks in accordance with an illustrative embodiment. The process illustrated in FIG. 26 may be implemented in a digital life recording system, such as digital life recording system 300 shown in FIG. 3.

The process begins by monitoring for a connection associated with a new infrastructure network (step 2600). The connection may be established either by wired or wireless means. In response to detecting a connection, the process verifies infrastructure network connectivity (step 2602). The process then retrieves configuration information to determine the types of feeds to acquire (step 2604). The types of feeds may include, but are not limited to, feeds containing data associated with weather conditions and feeds containing data associated with road conditions.

The process connects to the desired feeds (step 2606) and polls the infrastructure feeds for content (step 2608). In response to receiving data/content from the infrastructure feeds, the data is tagged with the content source information, a timestamp and global positioning system location (step 2610). The process sends the tagged data to the raw data queue (step 2612).

The process determines whether the retrieved data contains data associated with road warnings or weather warnings related to the current location of the person (step 2614). In response to a determination that the retrieved data contains data associated with road warnings or weather warnings related to the current location of the person, the road warning/weather warning is sent to a personal audio and video playback subsystem for announcing the warning(s) to the person (step 2616).

The process determines whether more data exists in the connected infrastructure feeds (step 2618). In response to a determination that more data exists in the connected infrastructure feeds, the process repeats the steps of polling (step 2608) and tagging the data (step 2610), sending the tagged data to the raw data queue (step 2612), and determining whether the data contains data associated with road warnings or weather warnings related to the current location of the person (step 2614).

In response to a determination that more data does not exist in the connected infrastructure feeds, the process returns to the step of monitoring for a connection associated with a new infrastructure network (step 2600).

Figure 27:
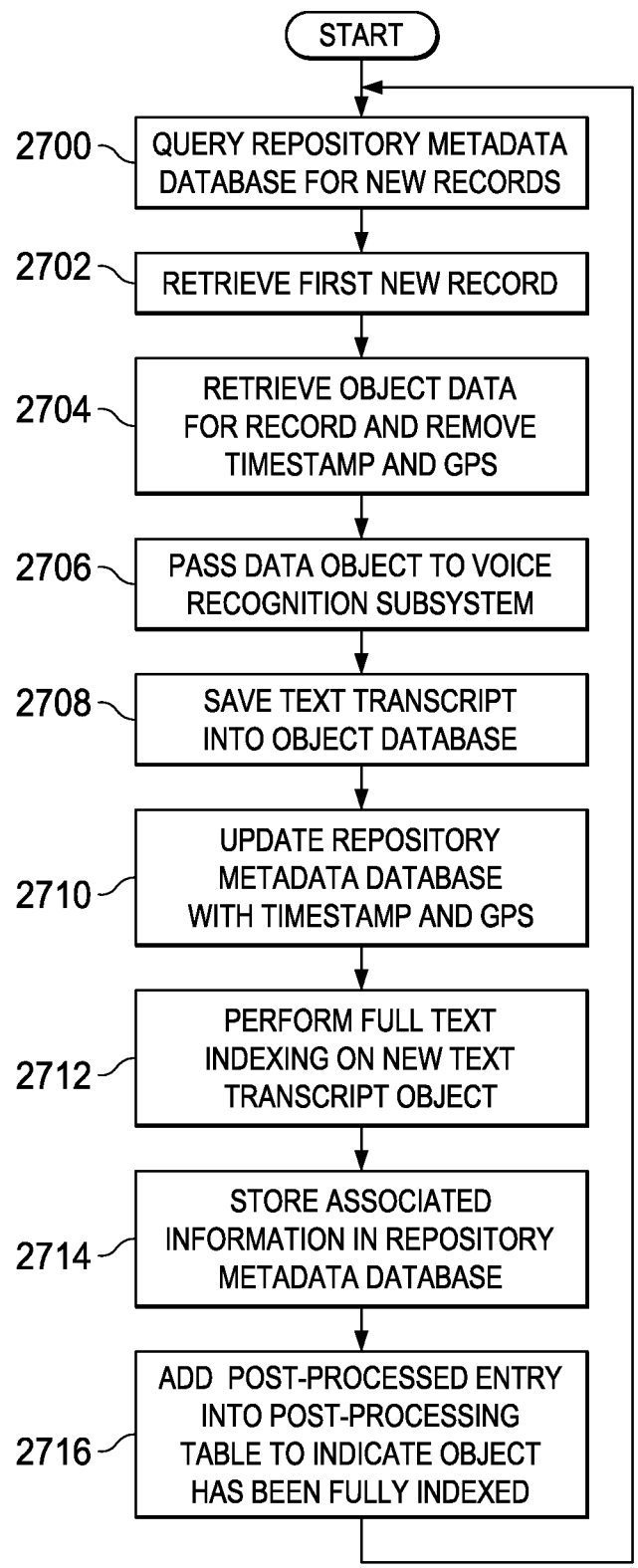
FIG. 27 is a flowchart of a process for improving the indexing of data stored in the repository mass store is depicted in accordance with an illustrative embodiment.

FIG. 27 is a flowchart of a process for improving the indexing of data stored in the repository mass store in accordance with an illustrative embodiment. The process illustrated in FIG. 27 may be implemented in a digital life recording system, such as digital life recording system 300 shown in FIG. 3.

The process begins by querying a repository metadata database, such as digital life metadata database 538 shown in FIG. 5, for new records (step 2700). In response to a determination that new records exist, the process retrieves the first new record (step 2702). The process retrieves the object data associated with the new record and retrieves the global positioning system (GPS) timestamp and location from the object data (step 2704). The process passes the data object to a voice recognition subsystem to generate a text transcript of the object data. (step 2706).

The process saves the text transcript into an object database (step 2708), such as digital life information object database 540 shown in FIG. 5. The process then updates the repository metadata database with the global positioning system (GPS) timestamp and location, a unique identifier that points to the physical location of the text object (step 2710). The process then performs full text indexing on the new text transcript object (step 2712). The process stores the information associated with the full text indexing in the repository metadata database (step 2714). The process adds a post-processed entry, for the text transcript object, into a post processing table to indicate that the associated text transcript object has been fully indexed (step 2716). The process loops and queries the repository metadata database for a new record (step 2700).

Figure 28:
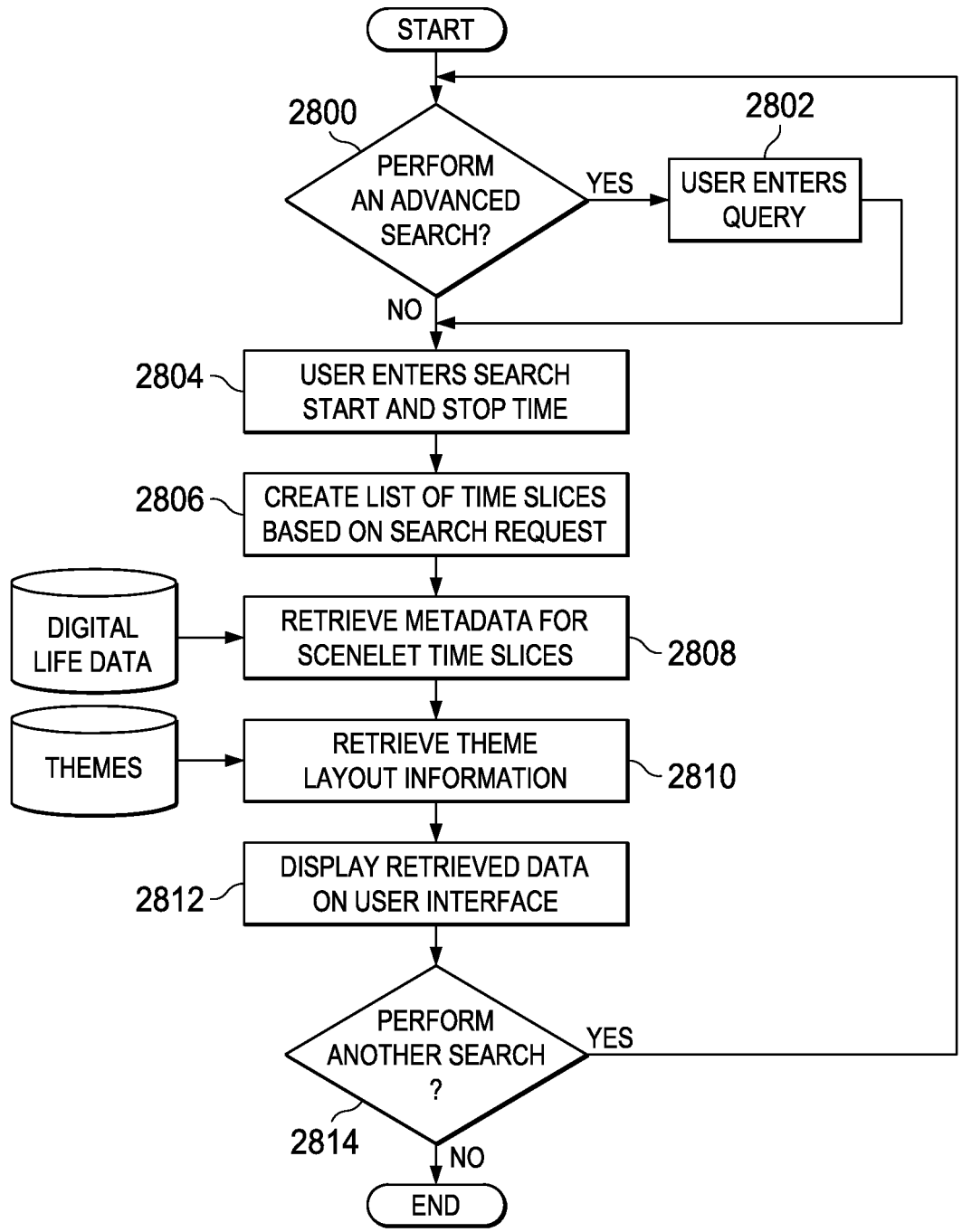
FIG. 28 is a flowchart of a process for searching, retrieving, and rendering data is depicted in accordance with an illustrative embodiment.

FIG. 28 is a flowchart of a process for searching, retrieving, and rendering data in accordance with an illustrative embodiment. The process illustrated in FIG. 28 may be implemented in a digital life recording system, such as digital life recording system 300 shown in FIG. 3.

The process begins by determining whether the user has selected an option to perform an advance search (step 2800). In an advance search, the process receives a query request from a user to query the repository database (step 2802). The query uses a database querying language, such as, but not limited to, structured query language (SQL). For a regular search, the process receives a request from a user containing a starting date/time and an ending date/time (step 2804). The process creates a list of time slices based on the search request (step 2806).

The process retrieves metadata for the scenelet time slices from a digital life data repository (step 2808), such as digital life data repository 804 shown in FIG. 8. The process also retrieves metadata for non-video information, such as, but not limited to, audio and temperature. The process then retrieves theme layout information from a themes database (step 2810), such as themes database 818 shown in FIG. 8. The process displays the retrieved data on a user interface (step 2812), such as user interface 900 shown in FIG. 9. The process then determines whether another search request is to be performed (step 2814). In response to determining that another search request is to be performed, the process loops back to step 2800.

Figure 29:
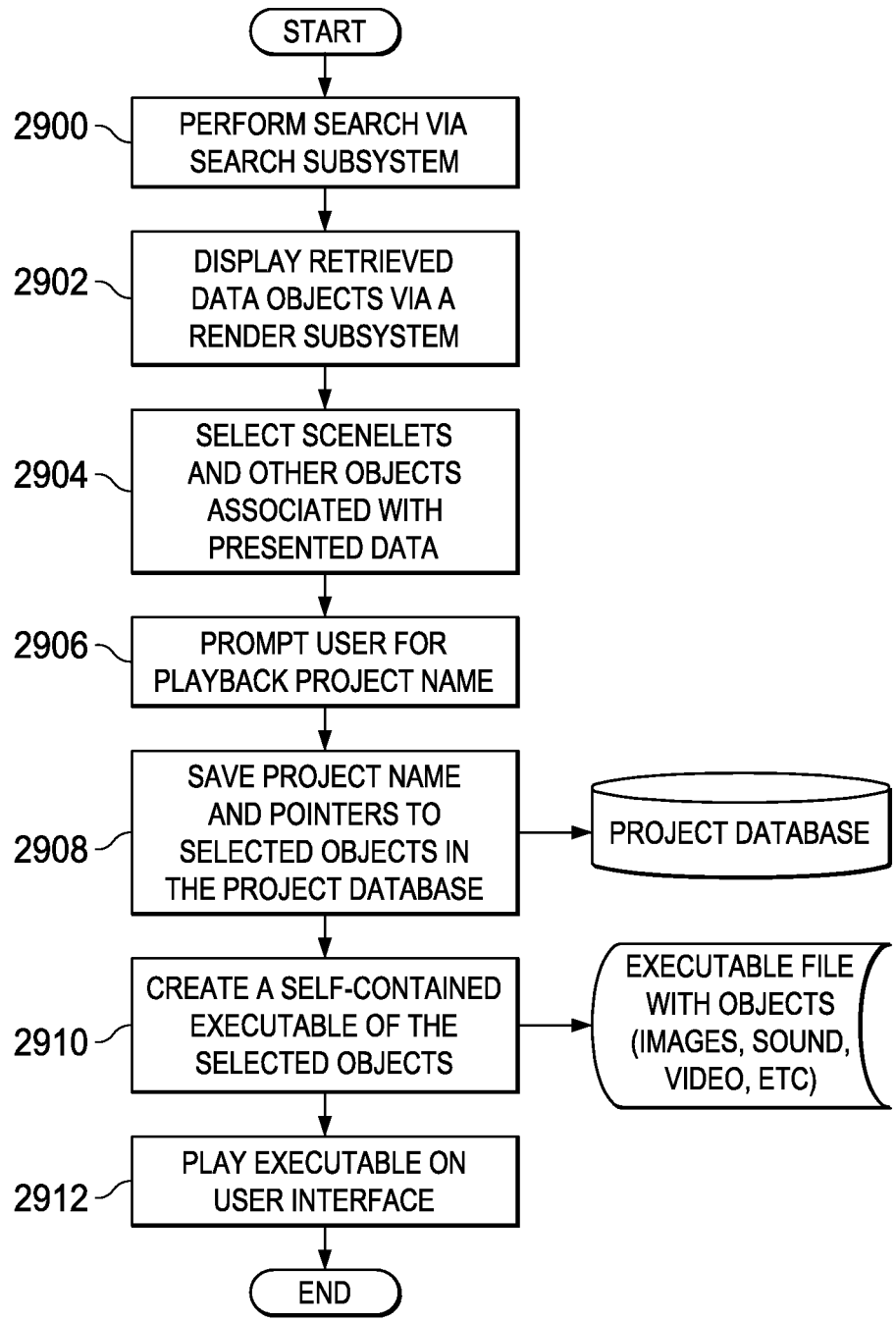
FIG. 29 is a flowchart of a process for organizing and presenting data is depicted in accordance with an illustrative embodiment.

FIG. 29 is a flowchart of a process for organizing and presenting data in accordance with an illustrative embodiment. The process illustrated in FIG. 29 may be implemented in a digital life recording system, such as digital life recording system 300 shown in FIG. 3.

The process begins by performing a search for data objects via a search subsystem (step 2900), such as search subsystem 812 shown in FIG. 8. The process displays the retrieved data objects via a render subsystem (step 2902), such as render subsystem 814 shown in FIG. 8. The process selects scenelets and other objects associated with presented data (step 2904).

The process then prompts a user for a playback project name (step 2906). In response to receiving a project name from a user, the process saves the project name and pointers to the selected objects in a project definitions database (step 2908), such as project definitions database 858 shown in FIG. 8. A pointer is a variable that holds the address of a data object or function.

The process then creates a self-contained executable of the selected objects (step 2910). The self-contained executable may be emailed, posted to a web-site, or saved in non-volatile memory, such as on a hard drive. In response to a receiving a request to execute the self-contained executable of the selected objects, the process plays the self-contained executable on a user interface (step 2912), such as user interface 900 shown in FIG. 9.

Figure 30:
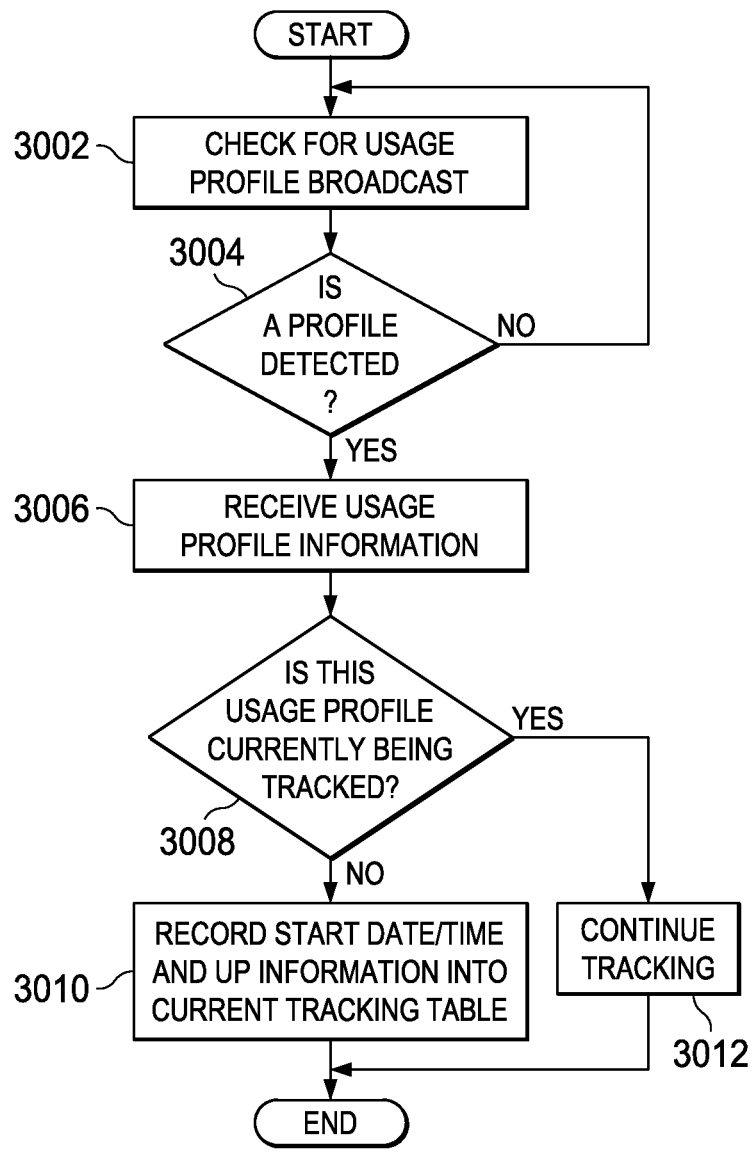
FIG. 30 is a flowchart of a process for detecting a new user profile in accordance with an illustrative embodiment.

FIG. 30 is a flowchart illustrating a process for detecting a new user profile in accordance with an illustrative embodiment. The process depicted in FIG. 30 may be implemented by a system, such as digital life recorder 300 in FIG. 3, usage profile environment 1100 in FIG. 11, or usage profile environment 1200 in FIG. 12.

Process 3000 begins by checking for a broadcast of a usage profile (step 3002). A usage profile sensor determines whether there is a usage profile being broadcasted (step

3004). If there is not a broadcast, a usage profile sensor keeps checking for a broadcast. If there is a broadcast, a usage profile sensor receives the broadcast of the usage profile (step 3006). The usage profile can comprise a usage policy.

The process 3000 then determines whether the usage profile detected is currently being tracked (step 3008). To determine whether the usage profile is being tracked, the usage profile processor can check the tracking table. If the usage profile is not being tracked, the usage profile processor will record the current date and time as the start date and time and the usage profile processor will record the usage profile information into the tracking table (step 3010). If the usage profile is being tracked, the usage profile processor will continue tracking the usage profile (step 3012). Thereafter the process terminates.

Figure 31:
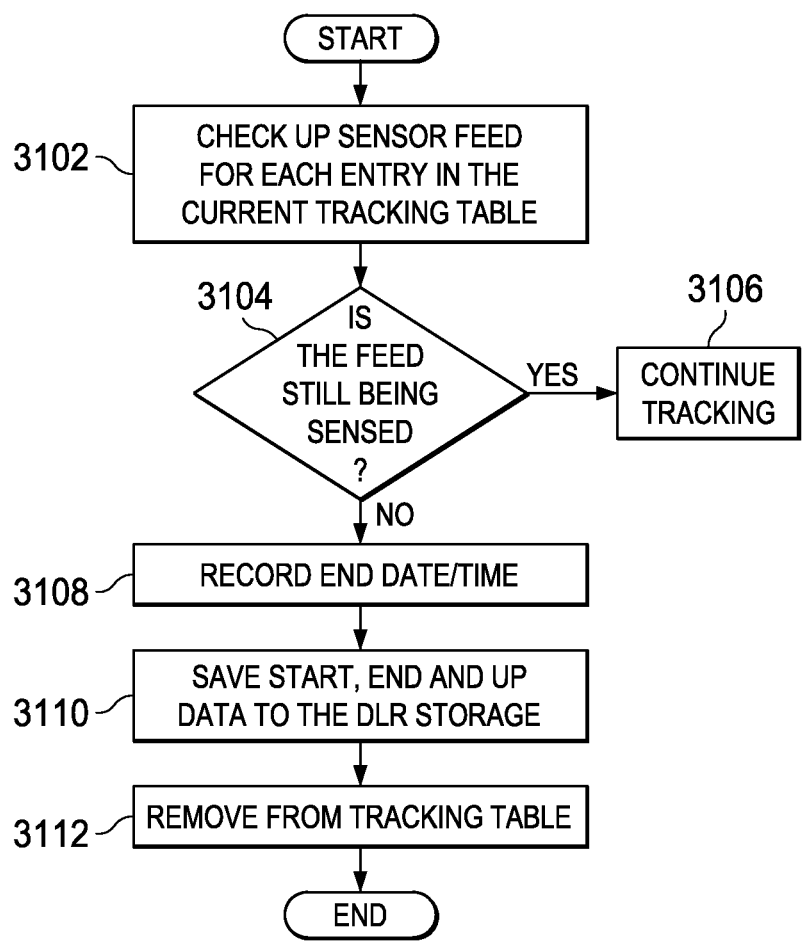
FIG. 31 is a flowchart of a process for detecting whether a tracked user profile is still being tracked in accordance with an illustrative embodiment.

FIG. 31 is a flowchart illustrating a process for detecting a whether a tracked user profile is still being tracked in accordance with an illustrative embodiment. The process depicted in FIG. 31 may be implemented by a system, such as digital life recorder 300 in FIG. 3, usage profile environment 1100 in FIG. 11, or usage profile environment 1200 in FIG. 12.

Process 3100 begins by checking for a broadcast of a usage profile (step 3102). A usage profile sensor determines whether there is a usage profile being broadcasted for each usage profile listed in the tracking table (step 3104). If there is a broadcast, the usage profile processor keeps tracking the usage profile that is still being broadcasted (step 3106). If there is not a broadcast, the usage profile processor records the current time as the end date and the end time in the tracking table for the usage profile that is no longer being broadcasted (step 3108).

Then, the usage profile processor saves the start date and time, the end date and time, and the usage profile to the digital life recorder storage (step 3110). Once the information has been saved, the usage profile processor removes the information from the tracking table (step 3112). Thereafter the process terminates.

Thus, the illustrative embodiments described herein provide a computer implemented method, apparatus, and computer program product for managing data. Data capturing devices dynamically capture data associated with the daily activities of a person. The data is processed using a mobile device associated with the person. The data is stored into a cache of the mobile device. The data stored in the cache of the mobile device is uploaded into a repository mass store in response to interfacing the mobile device with the repository mass store. A selected data segment stored in the repository mass store is presented in response to receiving a request for the selected data segment.

The illustrative embodiments dynamically capture all aspects of daily activities associated with a person using a plurality of data capturing devices. Additionally, the illustrative embodiments captures data from external sources, such as, but not limited to, other people's life data recording system, public and private internet feeds, and information captured from broadcasts associated with businesses. Furthermore, the illustrative embodiments capture biometric data associated with the person including, but not limited to, temperature, heart rate, and blood pressure.

The illustrative embodiments present methods for capturing, organizing, and presenting the data in an efficient method. A person is able to digitally save all or any aspect and/or experience of the person's life for future viewing. Additionally, the data can be shared with other people, such as friends and family, or be archived for future generations to experience.

The illustrative embodiments determine whether a broadcast of a usage profile is detected. The illustrative embodiments receive the broadcast of the usage profile in response to a first determination that the broadcast of the usage profile is detected, wherein the usage profile comprises a usage policy. The illustrative embodiments determine whether the usage profile is currently being tracked. The illustrative embodiments record a start date, a start time, and usage profile information into a tracking table in response to a second determination that the usage profile is not currently being tracked.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories, which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method for managing usage policies for live data recorded with a digital life recorder, the computer implemented method comprising:

monitoring continuously by a usage profile sensor for a broadcast of a usage profile including a usage policy from a usage profile notifier in a usage profile environment including multiple broadcasts, multiple usage profiles and multiple usage profile sensors;

responsive to detecting the broadcast by detecting the digital life recorder entering within a geographical range of the broadcast, determining whether the usage profile of the broadcast detected is currently being tracked by checking a tracking table, wherein a usage profile processor tracks each usage profile individually, and wherein a completed entry in the tracking table contains information comprising a start date and a start time, an end date and an end time and a particular usage profile, and wherein the tracking table is maintained in a daily cache comprising a digital life metadata database and digital life information object database;

responsive to a determination the usage profile of the broadcast detected is not currently being tracked, recording a current date and time as the start date and the start time, at which the broadcast of the usage policy was received, and the particular usage profile into the tracking table;

recording the live data by a camera and an audio capturing device connected to the digital life recorder positioned on a user while continuously receiving, at the digital life recorder, the broadcast over a wireless network of the usage policy for the live data currently being recorded, wherein the broadcast of the usage policy from an individual or organization has the geographical range, wherein the live data recorded with the digital life recorder includes audio data and video data, wherein the usage policy includes information broadcast from the individual or the organization other than the user of the digital life recorder, including policy information comprising a definition of how a person wants a respective image and conversation used, a definition of how a building or location wants recordings in the building or location used and a definition of how a content provider wants content rebroadcast, and usage restrictions including conditions on how images from the live data recorded with the digital life recorder and associated with the individual or the organization can be transferred by the user;

responsive to no longer detecting the broadcast of the usage policy by detecting the digital life recorder is not within the geographical range of the broadcast, recording the current date and time as the end date and the end time, at which the broadcast of the usage profile including the usage policy was no longer detected, into the tracking table;

identifying portions of the live data to be restricted by the usage policy by identifying portions of the live data recorded by one of the camera and the audio capturing device while the digital life recorder was within the geographical range of the broadcast between the start time and the end time of the usage policy of the usage profile recorded in the tracking table to form the portions of the live data to be restricted by the usage policy; and submitting the usage profile, the start time, and the end time from the tracking table in the daily cache to a digital life recorder storage in a digital life repository subsystem for later use.

2. The computer implemented method of claim 1 further comprising:

associating the usage policy of the usage profile being currently tracked with the live data currently being recorded; and storing the live data currently being recorded in association with the usage profile.

3. The computer implemented method of claim 1 further comprising:

responsive to saving the start date, the start time, usage profile information, the end date, and the end time to a digital life recorder storage, removing the start date, the start time, the usage profile information, the end date, and the end time from the tracking table.

4. The computer implemented method of claim 1 wherein determining whether the usage profile is being tracked further comprises:

detecting the start date, the start time, and the usage profile in the tracking table for the usage profile broadcasted including the usage policy.

5. A non-transitory computer readable storage medium storing a computer program product comprising computer usable program code for managing digital life recording data, for execution on a computer, the computer program product comprising:

computer usable program code for monitoring continuously by a usage profile sensor for a broadcast of a usage profile including a usage policy from a usage profile notifier in a usage profile environment including multiple broadcasts, multiple usage profiles and multiple usage profile sensors;

computer usable program code responsive to detecting the broadcast by detecting the digital life recorder entering within a geographical range of the broadcast, for determining whether the usage profile of the broadcast detected is currently being tracked by checking a tracking table, wherein a usage profile processor tracks each usage profile individually, and wherein a completed entry in the tracking table contains information comprising a start date and a start time, an end date and an end time and a particular usage profile, and wherein the tracking table is maintained in a daily cache comprising a digital life metadata database and digital life information object database;

computer usable program code responsive to a determination the usage profile of the broadcast detected is not currently being tracked, for recording a current date and time as the start date and the start time, at which the broadcast of the usage policy was received, and the particular usage profile into the tracking table;

computer usable program code for recording live data by a camera and an audio capturing device connected to the digital life recorder positioned on a user while continuously receiving, at the digital life recorder, the broadcast over a wireless network of the usage policy for the live data currently being recorded, wherein the broadcast of the usage policy from an individual or organization has the geographical range, wherein the live data recorded with the digital life recorder includes audio data and video data, wherein the usage policy includes information broadcast from the individual or the organization other than the user of the digital life recorder, including policy information comprising a definition of how a person wants a respective image and conversation used, a definition of how a building or location wants recordings in the building or location used and a definition of how a content provider wants content rebroadcast, and usage restrictions including conditions on how images from the live data recorded with the digital life recorder and associated with the individual or the organization can be transferred by the user;

computer usable program code for responsive to no longer detecting the broadcast of the usage policy by detecting the digital life recorder is not within the geographical range of the broadcast, recording the current date and time as the end date and the end time that the broadcast of the usage policy was no longer detected into the tracking table;

computer usable program code for identifying portions of the live data to be restricted by the usage policy by identifying portions of the live data recorded by one of the camera and the audio capturing device while the digital life recorder was within the geographical range of the broadcast between the start time and the end time of the usage policy of the usage profile recorded in the tracking table to form the portions of the live data to be restricted by the usage policy; and computer usable program code for submitting the usage profile, the start time, and the end time from the tracking table in the daily cache to a digital life recorder storage in a digital life repository subsystem for later use.

6. The computer program product of claim 5 further comprising:

computer usable program code for associating the usage policy of the usage profile being currently tracked with the live data currently being recorded; and computer usable program code for storing the live data currently being recorded in association with the usage profile.

7. The computer program product of claim 5 further comprising:

computer usable program code responsive to saving the start date, the start time, usage profile information, the end date, and the end time to a digital life recorder storage, for removing the start date, the start time, the usage profile information, the end date, and the end time from the tracking table.

8. The computer program product of claim 5 wherein the computer usable program code for determining whether the usage profile is being tracked further comprises:

computer usable program code for detecting the start date, the start time, and the usage profile in the tracking table for the usage profile broadcasted including the usage policy.

9. An apparatus comprising:

a bus system;

a communications system connected to the bus system;

a memory connected to the bus system, wherein the memory includes computer usable program code;

a digital life recorder connected to the communications system; and a processing unit connected to the bus system, wherein the processing unit is configured to execute the computer usable program code to:

monitor continuously by a usage profile sensor for a broadcast of a usage profile including a usage policy from a usage profile notifier in a usage profile environment including multiple broadcasts, multiple usage profiles and multiple usage profile sensors;

responsive to detecting the broadcast by detecting the digital life recorder entering within a geographical range of the broadcast, determine whether the usage profile of the broadcast detected is currently being tracked by checking a tracking table, wherein a usage profile processor tracks each usage profile individually, and wherein a completed entry in the tracking table contains information comprising a start date and a start time, an end date and an end time and a particular usage profile, and wherein the tracking table is maintained in a daily cache comprising a digital life metadata database and digital life information object database;

responsive to a determination the usage profile of the broadcast detected is not currently being tracked, record a current date and time as the start date and the start time, at which the broadcast of the usage policy was received, and the particular usage profile into the tracking table;

record live data by a camera and an audio capturing device connected to the digital life recorder positioned on a user while continuously receiving, at the digital life recorder, the broadcast over a wireless network of the usage policy for the live data currently being recorded, wherein the broadcast of the usage policy from an individual or organization has the geographical range, wherein the live data recorded with the digital life recorder includes audio data and video data, wherein the usage policy includes information broadcast from the individual or the organization other than the user of the digital life recorder, including policy information comprising a definition of how a person wants a respective image and conversation used, a definition of how a building or location wants recordings in the building or location used and a definition of how a content provider wants content rebroadcast, and usage restrictions including conditions on how images from the live data recorded with the digital life recorder and associated with the individual or organization can be transferred by the user;

responsive to no longer detecting the broadcast of the usage policy by detecting the digital life recorder is not within the geographical range of the broadcast, record the current date and time as the end date and the end time, at which the broadcast of the usage profile including the usage policy was no longer detected into the tracking table;

identify portions of the live data to be restricted by the usage policy by identifying portions of the live data recorded by one of the camera and the audio capturing device while the digital life recorder was within the geographical range of the broadcast between the start time and the end time of the usage policy of the usage profile recorded in the tracking table to form the portions of the live data to be restricted by the usage policy; and submitting the usage profile, the start time, and the end time from the tracking table in the daily cache to a digital life recorder storage in a digital life repository subsystem for later use.

10. The apparatus of claim 9, wherein the processing unit is further configured to execute the computer usable program code to associate the usage policy of the usage profile being currently tracked with the live data currently being recorded; and store the live data currently being recorded in association with the usage profile.

11. A usage policy system comprising:
a digital life recorder positioned on a user, wherein the digital life recorder is configured to record live data by a camera and an audio capturing device connected to the digital life recorder positioned on a user while continuously receiving, at the digital life recorder, a broadcast over a wireless network of a usage policy for the live data currently being recorded, wherein the broadcast of the usage policy from an individual or organization has a geographical range, wherein the live data recorded with the digital life recorder includes audio data and video data, wherein the usage policy includes information broadcast from the individual or the organization other than the user of the digital life recorder, including policy information comprising a definition of how a person wants a respective image and conversation used, a definition of how a building or location wants recordings in the building or location used and a definition of how a content provider wants content rebroadcast, and usage restrictions including conditions on how images from the live data recorded with the digital life recorder and associated with the individual or organization can be transferred by the user;

a processor associated with the digital life recorder, wherein the processor is configured to:

monitor continuously using a usage profile sensor for a broadcast of a usage profile including a usage policy from a usage profile notifier in a usage profile environment including multiple broadcasts, multiple usage profiles and multiple usage profile sensors;

responsive to detecting the broadcast by detecting the digital life recorder entering within a geographical range of the broadcast, determine whether the usage profile of the broadcast detected is currently being tracked by checking a tracking table, wherein a usage profile processor tracks each usage profile individually, and wherein a completed entry in the tracking table contains information comprising a start date and a start time, an end date and an end time and a particular usage profile, and wherein the tracking table is maintained in a daily cache comprising a digital life metadata database and digital life information object database; and responsive to a determination the usage profile of the broadcast detected is not currently being tracked, record a current date and time as the start date and the start time, at which the broadcast of the usage policy was received, and the particular usage profile into the tracking table;

responsive to detecting the broadcast of the usage policy by detecting the digital life recorder entering the geographical range of the broadcast, to record a start time that the broadcast of the usage policy was received into a tracking table, wherein the processor is further configured, responsive to no longer detecting the broadcast of the usage policy by detecting the digital life recorder is not within the geographical range of the broadcast, to record the current date and time as the end date and the end time, at which the broadcast of the usage profile including the usage policy was no longer detected into the tracking table; and wherein the processor is further configured to identify portions of the live data to be restricted by the usage policy by identifying the portions of the live data recorded by one of the camera and the audio capturing device while the digital life recorder was within the geographical range of the broadcast between the start time and the end time of the usage policy of the usage profile recorded in the tracking table to form the portions of the live data to be restricted by the usage policy; and submit the usage profile, the start time, and the end time from the tracking table in the daily cache to a digital life recorder storage in a digital life repository subsystem for later use.

12. The usage policy system of claim 11, further comprising:
a storage device, wherein the storage device stores the usage profile and stores the live data currently being recorded in association with the usage policy.

* * * * *